(12) United States Patent
Guggenheimer et al.

(10) Patent No.: US 10,905,458 B2
(45) Date of Patent: Feb. 2, 2021

(54) TISSUE-REMOVING CATHETER, TISSUE-REMOVING ELEMENT, AND METHOD OF MAKING SAME

(71) Applicant: Covidien LP, Mansfield, MA (US)

(72) Inventors: Ethan Andrew Guggenheimer, Minnetonka, MN (US); Victoria Schuman, Minneapolis, MN (US); Virgil Koski, Columbia Heights, MN (US); Benjamin Robert Fruland, Blaine, MN (US); Lucas Schneider, Champlin, MN (US)

( * ) Notice: Subject to any disclaimer, the term of this patent is extended or adjusted under 35 U.S.C. 154(b) by 969 days.

(21) Appl. No.: 15/175,755

(22) Filed: Jun. 7, 2016

(65) Prior Publication Data

US 2016/0354109 A1 Dec. 8, 2016

Related U.S. Application Data

(60) Provisional application No. 62/172,586, filed on Jun. 8, 2015.

(51) Int. Cl.
*A61B 17/3207* (2006.01)
(52) U.S. Cl.
CPC .......... *A61B 17/320758* (2013.01); *A61B 2017/320775* (2013.01); *A61B 2017/320791* (2013.01)
(58) Field of Classification Search
CPC .......... Y10T 408/8957; Y10T 408/899; Y10T 408/90; Y10T 408/901; Y10T 408/904; Y10T 408/9042; Y10T 408/9044; Y10T 408/9045; Y10T 408/9046; Y10T 408/90467; Y10T 408/90473; Y10T 408/905; Y10T 408/906; Y10T 408/909; Y10T 408/9093; Y10T 408/9095;
(Continued)

(56) References Cited

U.S. PATENT DOCUMENTS 4,729,763 A * 3/1988 Henrie ............ A61B 17/32075
604/22
4,925,216 A 5/1990 Steer
(Continued)

FOREIGN PATENT DOCUMENTS

EP 1 058 516 B1 11/2005
EP 1 158 910 B1 10/2007
(Continued)

*Primary Examiner* — Jocelin C Tanner
(74) *Attorney, Agent, or Firm* — Stinson LLP

(57) ABSTRACT

A tissue-removing catheter includes a tissue-removing element operatively connected to a drive shaft for rotation of the tissue-removing element about an axis of rotation in a cutting direction. A tissue-removing head of the tissue-removing element defines an annular cutting blade. In some embodiments, angularly spaced cutting teeth form the cutting blade. Inner shearing members extend radially inward from the cutting blade. As the tissue-removing element rotates in the cutting direction and advances axially through a body lumen, the annular cutting edge separates the tissue from the body lumen wall. Leading surfaces of the inner shearing members shear the separated tissue radially inwardly. In some embodiments, the tissue-removing element is an integrally formed, one-piece body made by removing material from a blank to form the cutting blade and inner shearing members.

17 Claims, 26 Drawing Sheets

(58) Field of Classification Search
CPC ....... A61B 2017/320024; A61B 2017/320791;
A61B 2017/320775; A61B 5/15126;
A61B 5/15132; A61B 2017/00526
See application file for complete search history.

(56) References Cited

U.S. PATENT DOCUMENTS

| | | | |
|---|---|---|---|
| 5,084,010 A | | 1/1992 | Plaia et al. |
| 5,351,595 A | | 10/1994 | Johnston |
| 5,507,760 A | * | 4/1996 | Wynne .............. A61B 17/32078 |
| | | | 606/159 |
| 5,651,781 A | | 7/1997 | Grace |
| 5,919,203 A | | 7/1999 | Husted et al. |
| 6,136,014 A | | 10/2000 | Sirimanne et al. |
| 6,451,036 B1 | | 9/2002 | Heitzmann et al. |
| 6,461,357 B1 | * | 10/2002 | Sharkey ............... A61B 18/148 |
| | | | 606/45 |
| 6,623,496 B2 | | 9/2003 | Snow et al. |
| 6,666,874 B2 | | 12/2003 | Heitzmann et al. |
| 6,685,707 B2 | | 2/2004 | Roman et al. |
| 6,997,934 B2 | | 2/2006 | Snow et al. |
| 7,171,798 B1 | | 2/2007 | Bernardy |
| 7,172,610 B2 | | 2/2007 | Heitzmann et al. |
| 7,666,134 B2 | | 2/2010 | Eriksson et al. |
| 7,842,058 B2 | | 11/2010 | Simpson et al. |
| 8,070,762 B2 | | 12/2011 | Escudero et al. |
| 8,215,533 B2 | | 7/2012 | Viola |
| 8,236,016 B2 | | 8/2012 | To et al. |
| 8,262,585 B2 | | 9/2012 | Thompson et al. |
| 8,308,746 B2 | | 11/2012 | Pravong et al. |
| 8,337,516 B2 | | 12/2012 | Escudero et al. |
| 8,361,094 B2 | | 1/2013 | To et al. |
| 8,469,981 B2 | | 6/2013 | Robertson et al. |
| 8,475,483 B2 | | 7/2013 | Schmitz et al. |
| 8,496,677 B2 | * | 7/2013 | Zhang ............ A61B 17/320783 |
| | | | 606/159 |
| 8,531,064 B2 | | 9/2013 | Robertson et al. |
| 9,028,520 B2 | * | 5/2015 | Taylor ..................... A61B 1/32 |
| | | | 606/190 |
| 9,603,618 B2 | * | 3/2017 | Grace .................. A61N 1/0573 |
| 9,687,266 B2 | * | 6/2017 | Moberg ......... A61B 17/320758 |
| 2002/0049438 A1 | * | 4/2002 | Sharkey ............. A61B 18/1402 |
| | | | 606/41 |
| 2002/0077642 A1 | | 6/2002 | Patel et al. |
| 2003/0014050 A1 | * | 1/2003 | Sharkey ............... A61B 18/148 |
| | | | 606/45 |
| 2004/0193150 A1 | * | 9/2004 | Sharkey ............. A61B 18/1402 |
| | | | 606/41 |
| 2007/0266833 A1 | | 11/2007 | Radziszewski et al. |
| 2008/0154296 A1 | * | 6/2008 | Taylor ..................... A61B 1/32 |
| | | | 606/190 |
| 2010/0256527 A1 | | 10/2010 | Lippert et al. |
| 2010/0256528 A1 | | 10/2010 | Lippert et al. |
| 2010/0256601 A1 | | 10/2010 | Lippert et al. |
| 2010/0256602 A1 | | 10/2010 | Lippert et al. |
| 2010/0256606 A1 | | 10/2010 | Lippert et al. |
| 2011/0054507 A1 | | 3/2011 | Batten et al. |
| 2011/0098711 A1 | | 4/2011 | Batten et al. |
| 2012/0022564 A1 | | 1/2012 | Batten et al. |
| 2012/0046679 A1 | | 2/2012 | Patel |
| 2012/0123352 A1 | * | 5/2012 | Fruland ................ A61B 5/0066 |
| | | | 604/264 |
| 2012/0296277 A1 | | 11/2012 | Summerville et al. |
| 2013/0096587 A1 | | 4/2013 | Smith et al. |
| 2014/0128893 A1 | * | 5/2014 | Guggenheimer ........................... |
| | | | A61B 17/320758 |
| | | | 606/159 |
| 2014/0171987 A1 | * | 6/2014 | Schneider .......... A61B 17/3207 |
| | | | 606/159 |
| 2014/0222045 A1 | * | 8/2014 | Schneider ...... A61B 17/320783 |
| | | | 606/159 |
| 2015/0258333 A1 | * | 9/2015 | Carver ................. A61N 1/0573 |
| | | | 606/129 |

FOREIGN PATENT DOCUMENTS

| | | |
|---|---|---|
| EP | 1 870 044 B1 | 7/2009 |
| EP | 1 957 134 B1 | 8/2011 |
| WO | 2007/067449 A2 | 6/2007 |
| WO | 2010/077692 A2 | 7/2010 |
| WO | 2010/121172 A1 | 10/2010 |
| WO | 2012/003430 A2 | 1/2012 |
| WO | 2013/049734 A1 | 4/2013 |
| WO | WO-2014151814 A1 * | 9/2014 ..... A61B 17/320016 |

* cited by examiner

TISSUE-REMOVING CATHETER, TISSUE-REMOVING ELEMENT, AND METHOD OF MAKING SAME

CROSS-REFERENCE TO RELATED APPLICATIONS

The present application claims the benefit of U.S. Provisional Application Ser. No. 62/172,586, filed Jun. 8, 2015, the entirety of which is hereby incorporated by references herein.

FIELD OF THE DISCLOSURE

The present disclosure generally relates to a tissue-removing catheter, tissue-removing element thereof, and method of making the tissue-removing element.

BACKGROUND OF THE DISCLOSURE

Catheters are used to remove unwanted tissue from the body. As an example, atherectomy catheters are used to remove material from a blood vessel to open the blood vessel and improve blood flow through the vessel.

SUMMARY OF THE DISCLOSURE

A tissue-removing catheter includes a tissue-removing element operatively connected to a drive shaft for rotation of the tissue-removing element about an axis of rotation in a cutting direction. The tissue-removing element has a tissue-removing head that defines an annular cutting blade. In some embodiments, angularly spaced cutting teeth form the annular cutting blade. Inner shearing members extend radially inward from the annular cutting blade. As the tissue-removing element rotates in the cutting direction and advances axially through a body lumen, the annular cutting edge engages tissue in the body lumen and separates the tissue from the body lumen wall. Leading surfaces of the inner shearing members engage the separated tissue and shear it radially inwardly. In some embodiments, the tissue-removing element is an integrally formed, one-piece body. In these embodiments, the tissue-removing element is made by removing material from a blank to form the cutting blade and inner shearing members.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION

Figure 1:
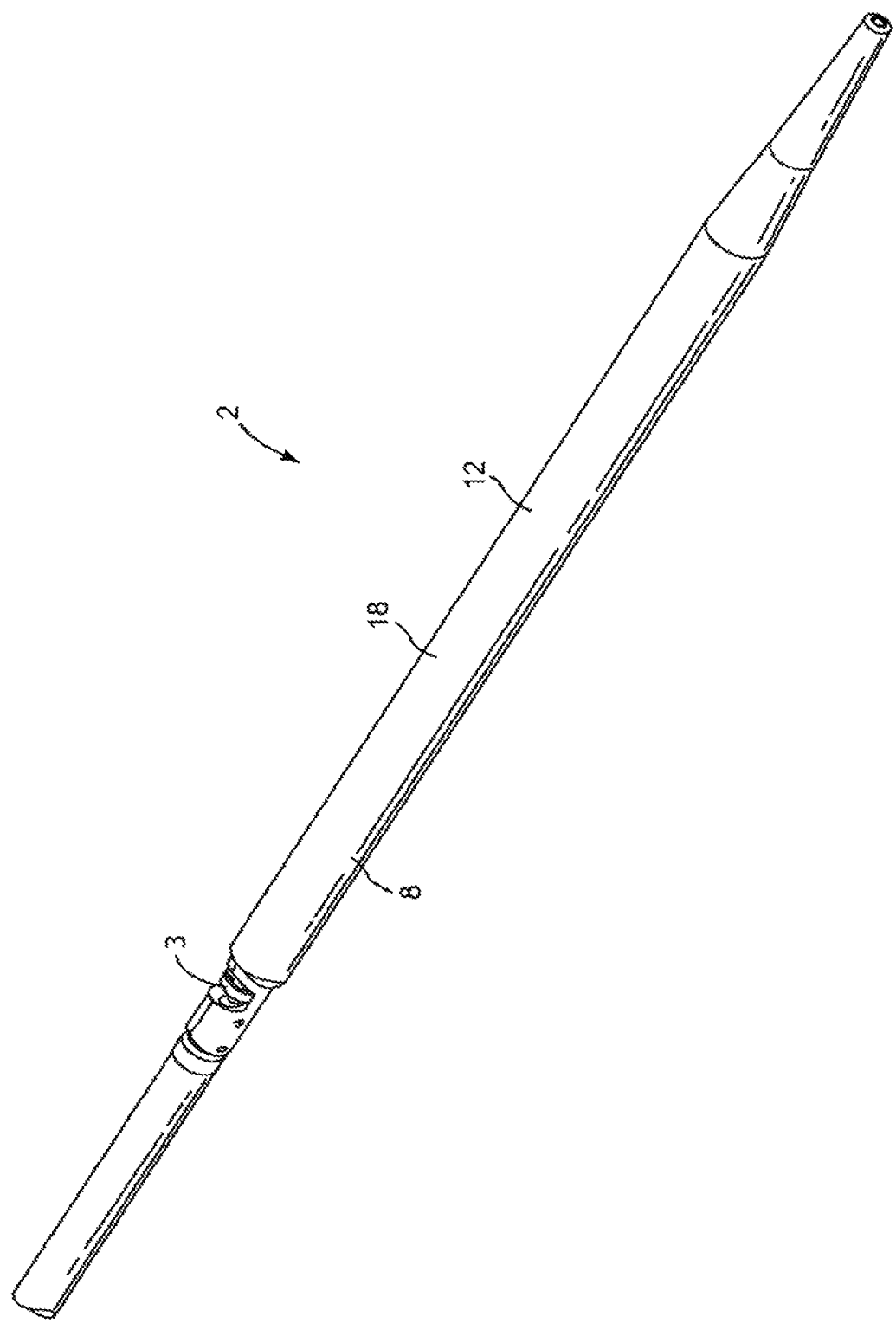
FIG. 1 is a perspective of a distal end of an atherectomy catheter.

Referring now to the drawings, several embodiments of a tissue-removing catheter for removing tissue from a body lumen are disclosed. In particular, the illustrated catheter embodiments are suitable for removing tissue from a body lumen wall, and are particularly suitable for removing (i.e., excising) plaque tissue from a vessel wall (e.g., peripheral arterial or peripheral venous wall). Features of the disclosed embodiments, however, may also be suitable for treating chronic total occlusion (CTO) of blood vessels, particularly peripheral arteries, and stenoses of other body lumens and other hyperplastic and neoplastic conditions in other body lumens, such as the ureter, the biliary duct, respiratory passages, the pancreatic duct, the lymphatic duct, and the like. Neoplastic cell growth will often occur as a result of a tumor surrounding and intruding into a body lumen. Removal of such material can thus be beneficial to maintain patency of the body lumen. While the remaining discussion is directed toward catheters for removing tissue from and penetrating occlusions in blood vessels (e.g., atheromatous or thrombotic occlusive material in an artery, or other occlusions in veins), it will be appreciated that the teachings of the present disclosure apply equally to other types of tissue-removing catheters, including, but not limited to, catheters for penetrating and/or removing tissue from a variety of occlusive, stenotic, or hyperplastic material in a variety of body lumens.

Figure 2:
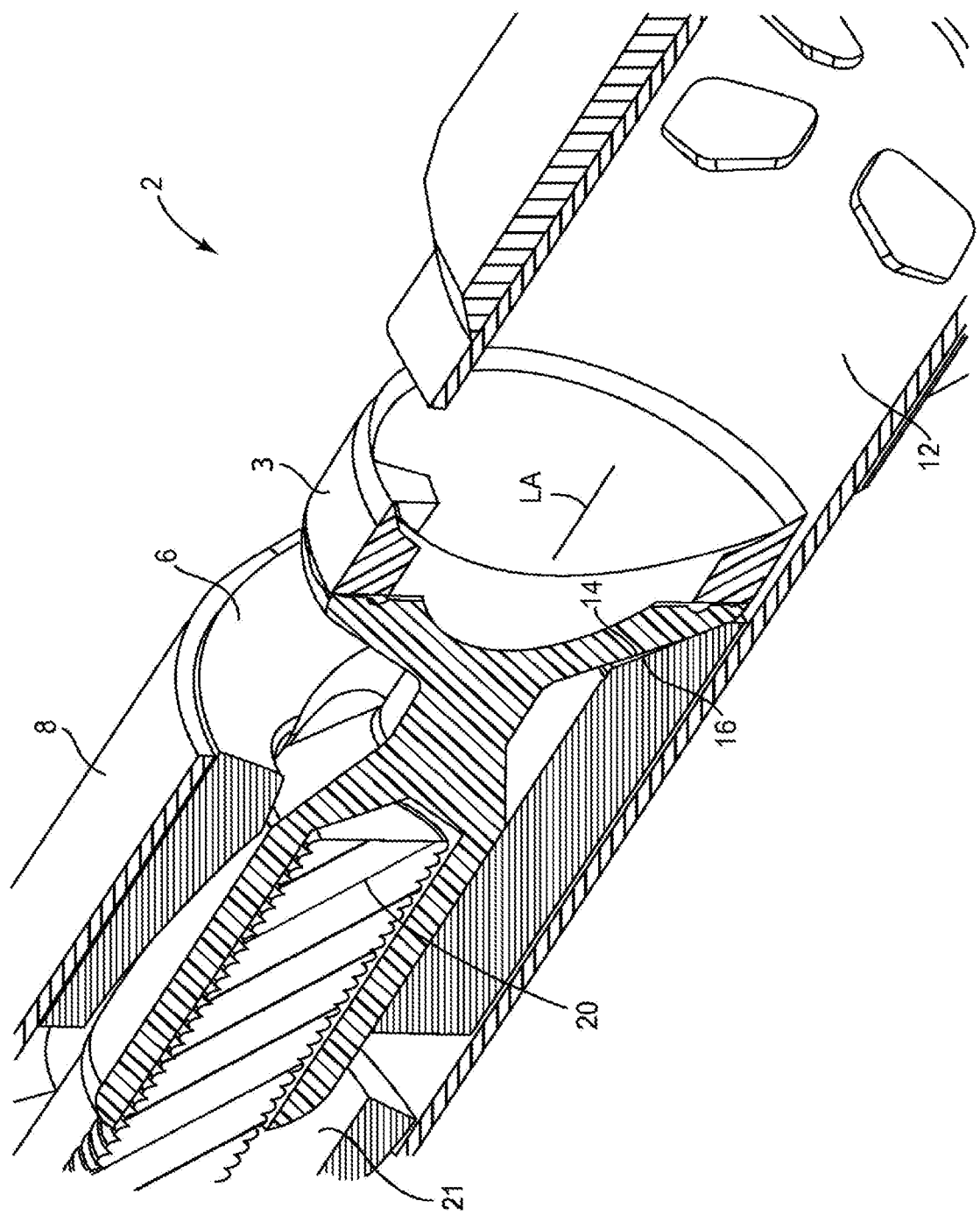
FIG. 2 is an enlarged fragmentary section of the atherectomy catheter of FIG. 1, illustrating a tissue-removing element in a stowed position.
Figure 3:
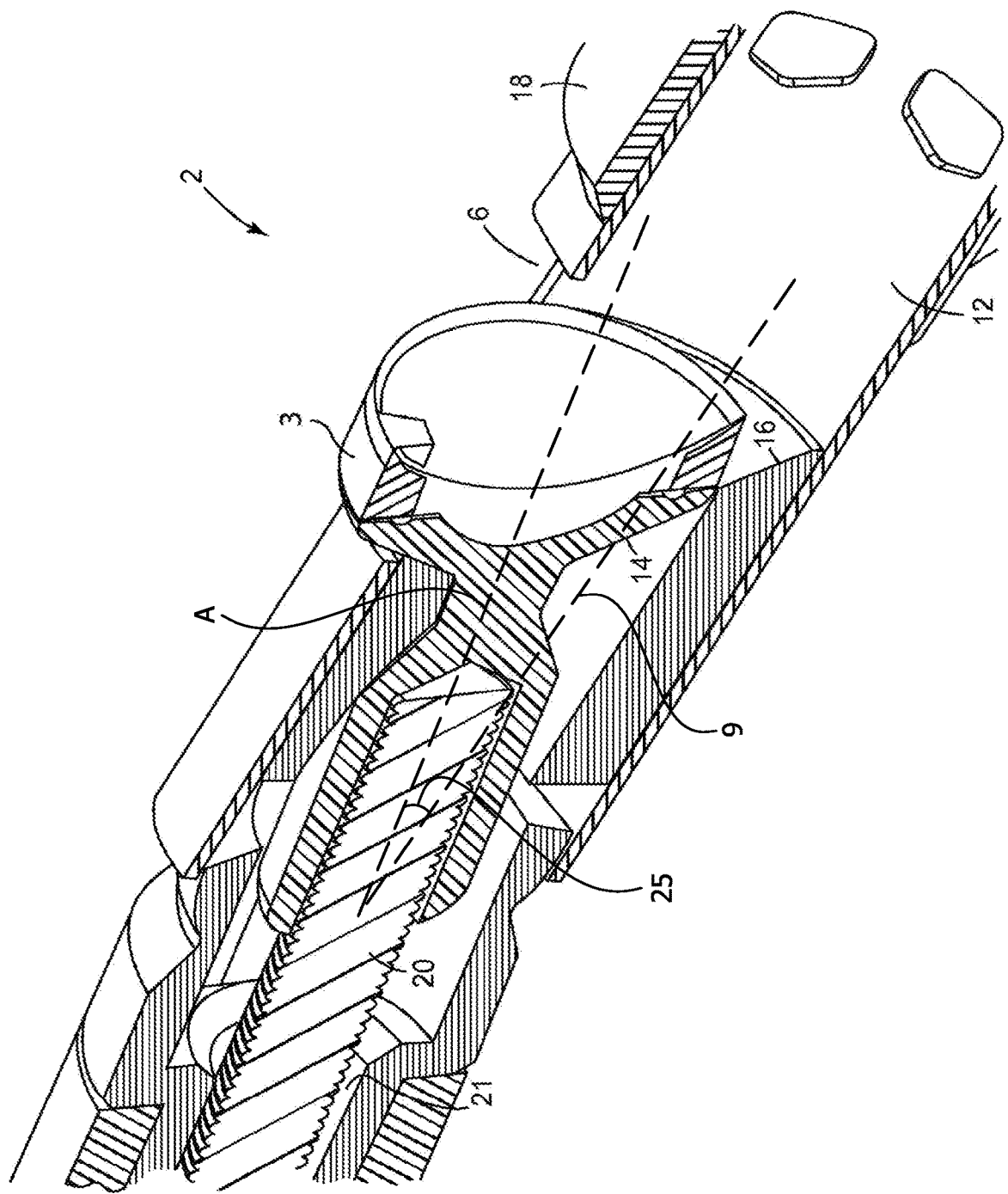
FIG. 3 is the enlarged fragmentary section of FIG. 1, illustrating the tissue-removing element in a deployed position.

Referring to FIGS. 1 to 3, an atherectomy catheter 2 (broadly, a "tissue-removing catheter"), which has a tissue-removing element 3 (broadly, a "tissue-removing element"), is used to cut material from a body lumen. The tissue-removing element 3 illustrated in FIGS. 1 to 3 is a conventional tissue-removing element. As will be explained below, tissue-removing element embodiments described in the present application are suitable replacements for the conventional tissue-removing element 3. That is, the tissue-removing element embodiments described herein below are suitable for use with the illustrated catheter 2 in place of the conventional tissue-removing element 3. The catheter has an elongate body 8 having distal and proximal portions and sized and shaped for insertion into a body lumen of a subject. The tissue-removing element 3 is movable between a stored position (FIG. 2) and a cutting position (FIG. 3) relative to a window or opening 6 in the catheter body 8 adjacent the distal portion. The tissue-removing element 3 moves outwardly relative to the opening 6 so that an exposed portion of the element 3 extends outside the body 8 through the opening 6. The tissue-removing element 3 may be positioned relative to the body 8 and opening 6 so that less than 90 degrees of the tissue-removing element 3 is exposed to cut tissue. Of course, more of the tissue-removing element 3 may be exposed without departing from numerous aspects of the invention. Preferably, when the tissue-removing element 3 is in the cutting position, a longitudinal axis A of the tissue-removing element 3 is oriented at an attack angle 25 relative a longitudinal axis 9 of a leading portion of the catheter body 8.

Catheter 2 may have a maximum size of 3, 4, 5, 6, 7, 8, 9, 10, or 12 French (1, 1.3, 1.7, 2, 2.3, 2.7, 3, 3.3, or 4 mm) and may have a working length ranging of 20, 30, 40, 60, 80, 100, 120, 150, 180 or 210 cm depending on the requirements of the anatomical location in which use of the catheter is contemplated.

In the illustrated embodiment, the catheter 2 is moved distally through a vessel with the tissue-removing element 3 in the working or cutting position as described in further detail below. As the catheter 2 moves through the blood vessel, the tissue is cut by the tissue-removing element 3 and is directed into a tissue chamber 12 positioned distal to the tissue-removing element 3. The tissue chamber 12 may be somewhat elongate to accommodate the tissue that has been cut.

Referring to FIG. 3, the illustrated tissue-removing element 3 is moved proximally from the stored position so that a cam surface 14 on the tissue-removing element 4 engages a ramp 16 on the body 8 of the catheter 2. The interaction between the cam surface 14 and the ramp 16 causes the tissue-removing element 3 to move to the cutting position and also causes a tip 18 to deflect which tends to move the tissue-removing element 3 toward the tissue to be cut. The tissue-removing element 3 may be deployed in other ways without departing from the scope of the present invention.

The tissue-removing element 3 is coupled to a drive shaft 20 that extends through a lumen 21 in the catheter 2. The tissue-removing element 3 is rotated about an axis of rotation A in a rotational direction R when the drive shaft rotates about its longitudinal axis. The tissue-removing element 3 may be rotated at about 1 to 160,000 rpm in use but may be rotated at any other suitable speed depending upon the particular application. Other ways of driving rotation of the tissue-removing element 3 do not depart from the scope of the present invention.

Figure 4:
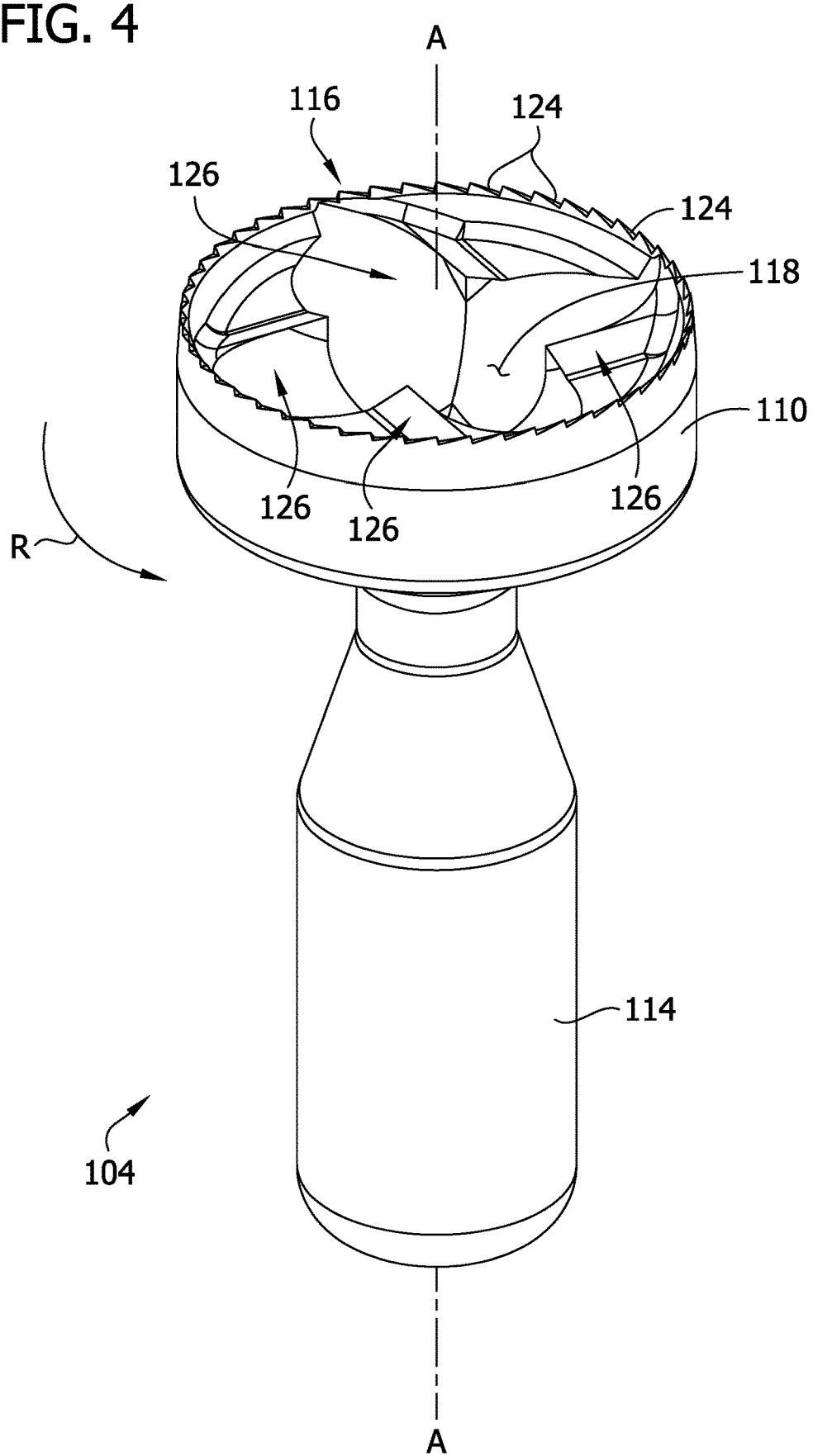
FIG. 4 is a perspective of another tissue-removing element.

Referring to FIG. 4, a first embodiment of a tissue-removing element suitable for use with the catheter 2 is generally indicated at reference number 104. The tissue-removing element 104 has proximal and distal axial ends (broadly, "first and second axial ends") spaced apart along an axis of rotation A. The tissue-removing element 104 includes a tissue-removing head, generally indicated at reference numeral 110, at the distal axial end thereof. A stem 114 of the tissue-removing element 4 connects the tissue-removing element to the drive shaft 20 for rotation about the axis of rotation A in a cutting direction R. The tissue-removing head 110 defines an annular toothed cutting blade, generally indicated at 116, that extends around the axis of rotation A. The cutting blade 116 extends generally axially in a distal direction (e.g., parallel to the axis of rotation A) so that the tissue-removing head 110 has a cup-shape that defines a recess 118. As discussed in further detail below, the cup-shape of the tissue-removing head 110 is operable to direct loose tissue in a body lumen toward the tissue collection chamber 12 as the catheter 2 advances axially through the lumen and the cutting element 104 rotates in the cutting direction R.

The cutting blade 116 comprises a plurality (e.g., 48) of cutting teeth 124 that are radially spaced from the axis of rotation A and angularly spaced from one another around the axis of rotation. As discussed in further detail below, as the cutting element 104 rotates in the cutting direction R and advances axially through a body lumen, the cutting teeth 124 cut into tissue in the body lumen. The cutting action of the teeth 124 is well-suited for slicing into soft tissue to separate the tissue from the luminal wall and for cleaving harder tissue by a grinding action. The many cutting teeth 124 of the cutting blade 116 enable substantially continuous engagement of the cutting blade with the tissue in the body lumen so that the cutting blade remains buried in the tissue as the tissue-removing element 104 rotates in the cutting direction R. In addition to the cutting teeth 124, the tissue-removing head 110 defines four inner shearing members 126 that are radially spaced from the axis of rotation A and angularly spaced from one another around the axis of rotation. As discussed in further detail below, as the cutting element 104 rotates in the cutting direction R and advances axially through the body lumen, the inner shearing members 126 cleave and impact the tissue to shear the tissue radially inwardly toward the axis of rotation A. The shearing action of the inner members 126 is particularly well-suited for removing hard tissue from the body lumen by fracturing it away from the luminal wall. Though the illustrated cutting element 4 includes 48 cutting teeth 124 and four inner shearing members 126, it will be understood that other numbers of cutting teeth and inner shearing members can be used without departing from the scope of the invention.

In the illustrated embodiment, the tissue-removing element 104 is integrally formed of one piece of material. Thus, the cutting teeth 124 and inner shearing members 126 are integrally formed of one piece of material. In other embodiments, it is contemplated that the tissue-removing element 104 can be a multi-piece assembly without departing from the scope of the invention. In one or more embodiments, the one-piece tissue-removing element 104 can be made from one of 465 stainless steel, 17-4 stainless steel, MP35N alloy, 35N LT alloy, titanium, and blends thereof. Other materials, such as other types of stainless steel, nickel, cobalt, chromium molybdenum, tungsten carbide, plastic, or combinations thereof, can also be used without departing from the scope of the invention. As discussed in further detail below, each cutting tooth 124, the inner shearing members 126, and the tissue-removing element body are preferably formed by removing material from a one-piece blank using a conventional machining process such as milling or Swiss machining.

Figure 5:
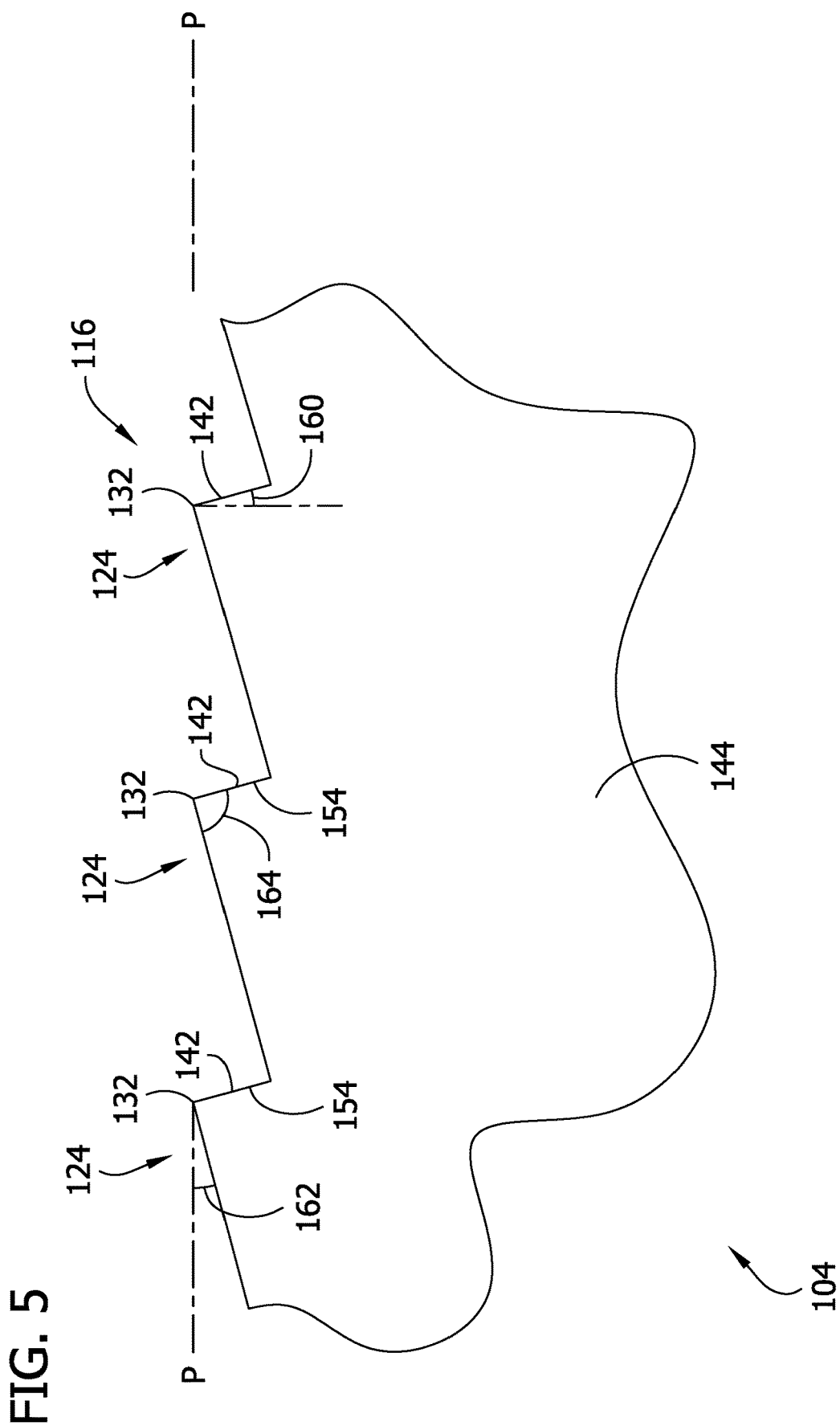
FIG. 5 is a fragmentary elevation of the tissue-removing element of FIG. 4.

In the illustrated embodiment, as shown in FIG. 5, distal tips 132 of each of the cutting teeth 124 are positioned in a cutting plane P oriented generally orthogonal to the axis of rotation A. Throughout the present disclosure, the cutting plane P of a tissue-removing element, such as the tissue-removing element 104, is a plane in which the distal tips (e.g., the tooth tips 132) of at least one and preferably at least two cutting components (e.g., the cutting teeth 124) are positioned. It is also contemplated that in other embodiments the distal tips of some of the cutting teeth may be axially offset from the cutting plane P so that only selected ones define the cutting plane. Generally, the cutting plane P will be oriented generally orthogonal to the axis of rotation A of the tissue-removing element 104. However, it is contemplated that the cutting plane can be oriented at another angle with respect to the axis of rotation A without departing from the scope of the invention.

Figure 6:
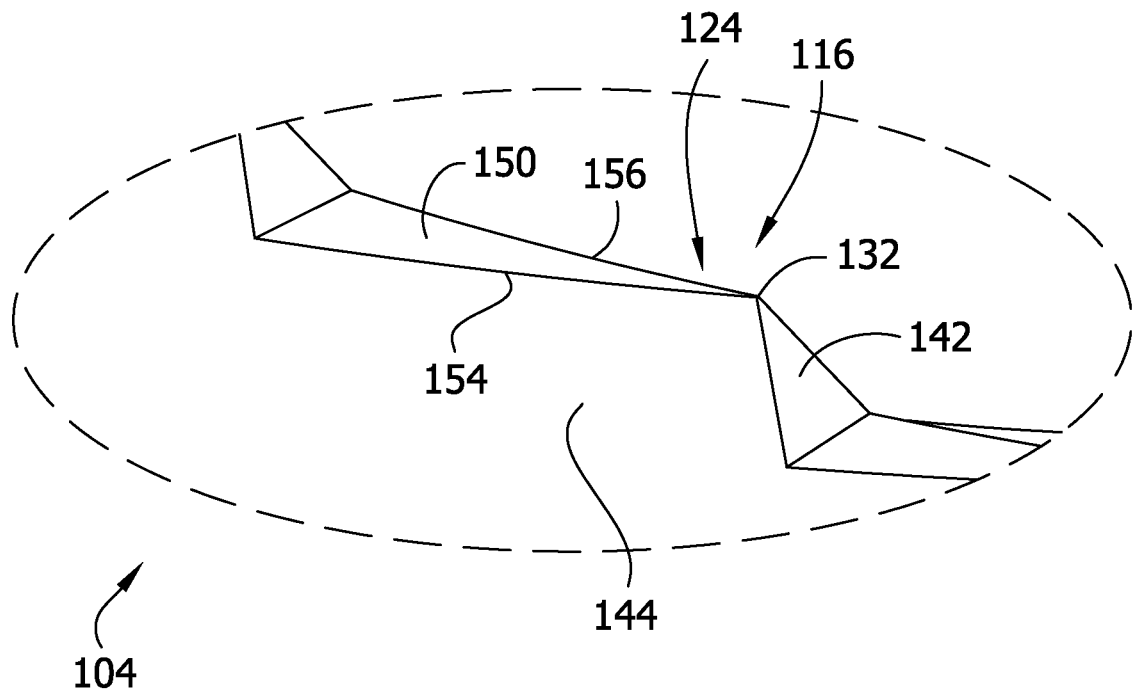
FIG. 6 is an enlarged fragmentary perspective of the tissue-removing element of FIG. 4.
Figure 7:
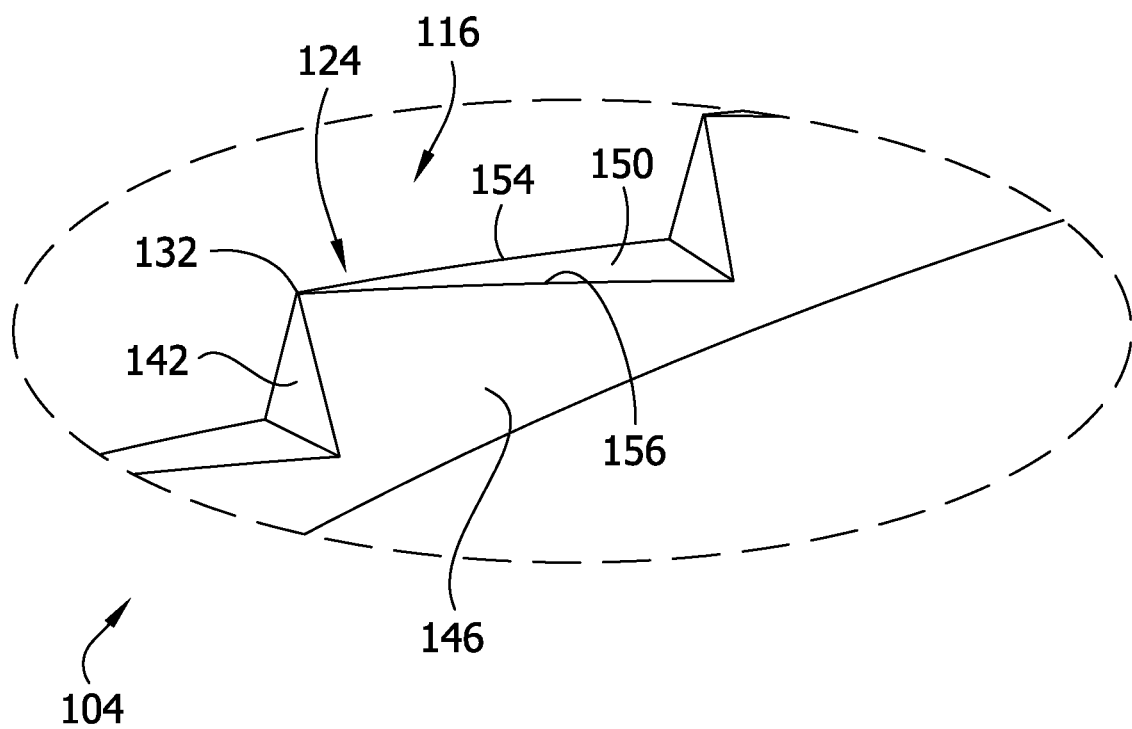
FIG. 7 is an enlarged fragmentary perspective of the tissue-removing element of FIG. 4.

Reference is now made to one of the cutting teeth 124 with the understanding that the description set forth below may apply equally to each of the cutting teeth. Although the illustrated embodiment uses cutting teeth 124 having substantially identical geometries, it will be understood that a cutting blade can include teeth with different geometries without departing from the scope of the invention. Referring to FIGS. 6 and 7, the cutting tooth 124 has a leading surface 142, a radially outer surface 144, and a radially inner surface 146, each of which extends generally axially outward in the distal direction at the distal end of the tissue-removing element 104. The leading surface 142 is at the forward or leading end of the cutting tooth 124 in the cutting direction R. An axial end surface 150 intersects the leading surface 142 at the distal tip 132 of the tooth 124 and intersects the radially outer and radially inner surfaces 144, 146 at respective radially outer, and radially inner edges 154, 156. The axial end surface 150 trails the leading surface 142 relative the cutting direction R.

The leading surface 142 of the cutting tooth 124 extends axially in the distal direction from the trailing end portion of the axial end surface 150 of the adjacent cutting tooth to the distal tip 132. Likewise, the leading surface 142 of the cutting tooth 124 extends radially between the radially outer surface 144 and the radially inner surface 146. Referring again to FIG. 5, the leading surface 142 of the cutting tooth 124 defines a rake angle 160 of the tooth. When viewed from a side elevation as in FIG. 5, the rake angle 160 of the cutting tooth 24 is measured as the angle between the leading surface 142 relative to a line orthogonal to the cutting plane P that passes through the distal tip 132. Each cutting tooth 124 may have a negative rake angle 160 because the leading surface 142 leads the line perpendicular to the cutting plane P in the cutting direction R. However, the rake angle 160 can also be positive (i.e., the leading surface 142 trails the line perpendicular to the cutting plane P in the cutting direction R) without departing from the scope of the invention.

In one or more preferred embodiments, the cutting tooth 124 has a rake angle 160 of between about −89° and about +30°. In the illustrated embodiment, the rake angle 160 is about −15°. The negative rake angle 160 prevents the cutting tooth 124 from hooking tissue as it rotates in the cutting direction R. In addition, the negative rake angle 160 prevents the cutting tooth 124 from engaging tissue too deeply or positively, which can cause the cutting blade 116 to climb out of the depression formed in the tissue as the tissue-removing element 4 rotates in the cutting direction R. The cutting blade 116 includes many cutting teeth 124 (e.g., more than eight) to provide consistent forces between the teeth and the tissue to reduce the likelihood of the cutting blade 116 climbing out of the depression formed in the tissue, which helps the blade continuously engage the tissue as the tissue-removing element 104 rotates in the cutting direction R. The small sizes of the teeth 124 provide an almost continuous surface of the tissue-removing element 104 that remains mechanically wedged beneath the tissue being cleaved, thereby ensuring consistent and substantially continuous engagement between the tissue and cutting blade 116. The use of many cutting teeth 124 also provides more opportunities to score the tissue and initiate cutting during each revolution of the tissue-removing element 104, especially with hard, smooth tissue, which helps the blade 116 initially engage the tissue as the tissue-removing element 104 rotates in the cutting direction R.

With further reference to FIG. 5, the cutting tooth 124 has a relief angle 162, which is the angle between the cutting plane P and the axial end surface 150 of the cutting tooth. An excessively large relief angle 162 may reduce the robustness of the cutting tooth 124 and cause the cutting tooth to engage tissue too deeply. An excessively small relief angle 162 might inhibit the tissue-removing element 104 from advancing axially through the body lumen at the desired rate because the cutting tooth 124 might not cut deeply enough into the tissue as it rotates. In one or more suitable embodiments, the relief angle 162 is between about 1° and about 90°. In the illustrated embodiment, the relief angle 162 is about 15°.

When the cutting tooth 124 is viewed from the side elevation as in FIG. 5, the leading surface 142 and the axial end surface 150 are oriented at a tooth angle 164 relative one another. To enhance manufacturability of the tissue-removing element 104, the relief angle 162 and rake angle 160 are preferably chosen to be equal in magnitude and opposite in sign so that the tooth angle 164 is about 90°. As discussed in further detail below, a tooth angle of about 90° enables a ninety-degree cutting implement (e.g., milling tool) to be used to form the axial end surface 150 and leading surface 142 of the cutting tooth 124 in a single pass.

Figure 8:
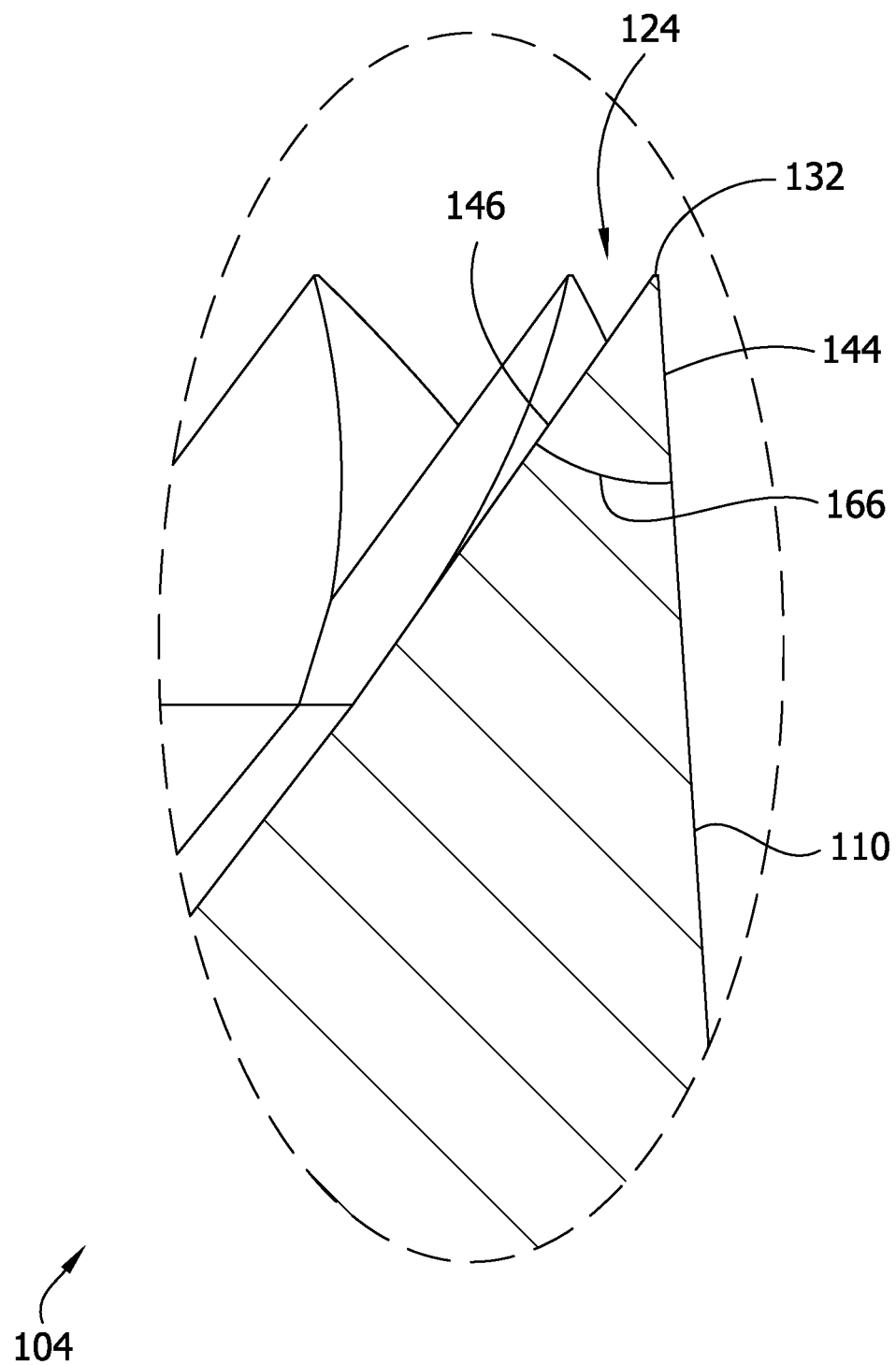
FIG. 8 is fragmentary section of the tissue-removing element of FIG. 4.

Referring to FIG. 8, the radially outer surface 144 of the cutting tooth 124, which extends generally axially (i.e., it does not slope substantially in a radial direction between its proximal and distal ends), is formed at a slight angle (e.g., from about 3° to about 15°) with the generally cylindrically shaped radially outer surface of the tissue-removing head 110. This slight angle provides some clearance as the tissue-removing element 104 moves between the stored and deployed positions. The radially inner surface 146 of the cutting tooth 124 slopes radially outwardly between its proximal and distal ends. The radially inner surface 146 is oriented at a wedge angle 166 relative the radially outer surface 144. In one or more preferred embodiments, the wedge angle 166 is between about 10° and about 80°. In the illustrated embodiment, the wedge angle 166 is about 40°. Thus, the cutting tooth 124 has a wedge-shaped cross-sectional shape that is wider at its proximal end than at the distal tip 132. As discussed in further detail below, the wedge-shaped cross-sectional shape of the cutting tooth 124 enables it to slice into soft tissue as the tissue-removing element 104 rotates in the cutting direction R and curl the tissue radially inwardly as the tissue-removing element 104 advances axially through the body lumen.

Figure 9:
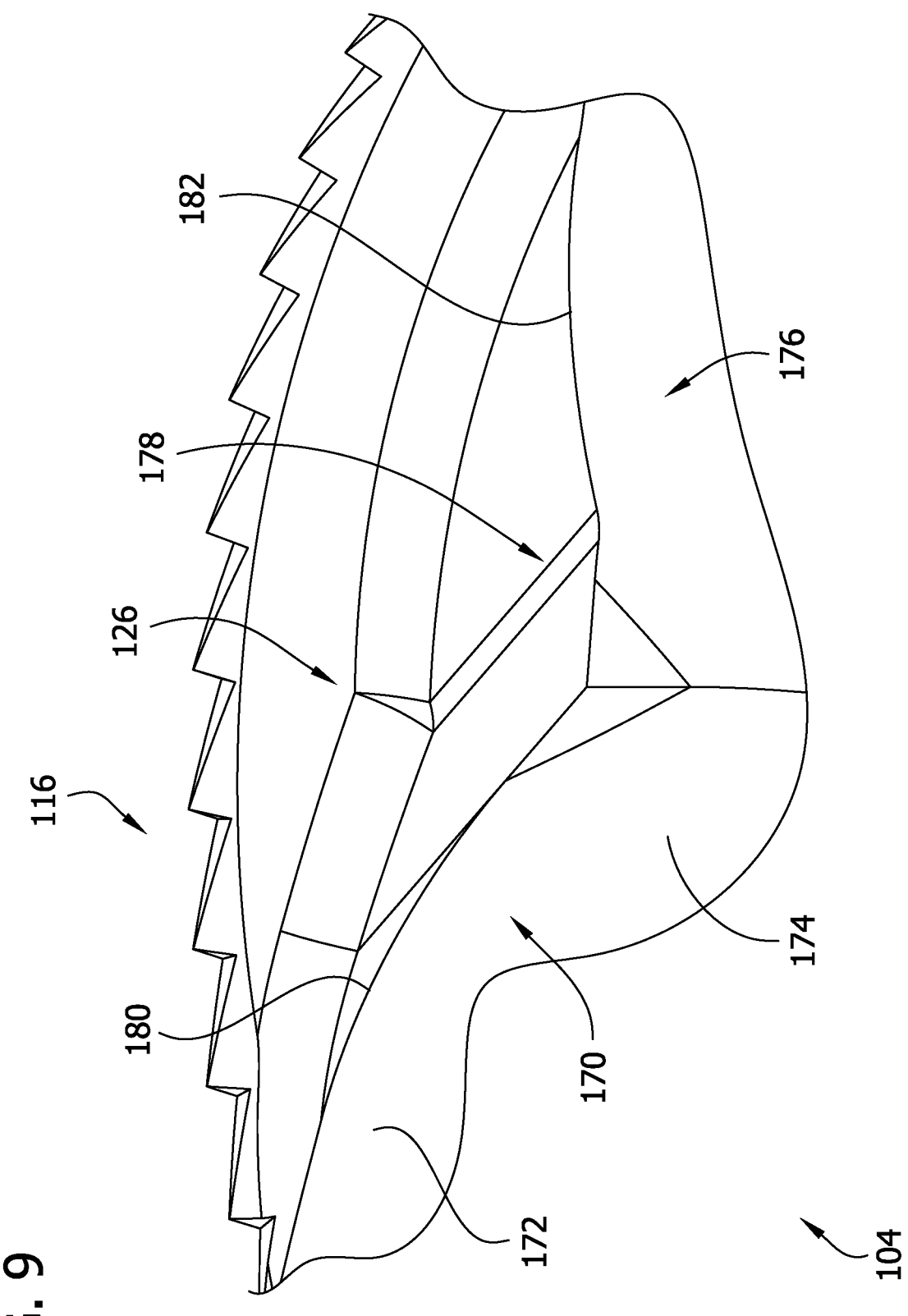
FIG. 9 is a fragmentary perspective of the tissue-removing element of FIG. 4.

Reference is now made to one of the inner shearing members 126, with the understanding that the description set forth below applies equally to each of the inner shearing members. Referring to FIG. 9, the inner shearing member 126 is adapted to impact tissue and shear it inwardly toward the central recess 118 as the tissue-removing element 4 rotates to facilitate removal of hard tissue. The inner shearing member has a leading surface, generally indicated at reference number 170. The leading surface 170 includes a radially outer, arcuate portion 172 that curves radially inward relative to the axis of rotation A, away from the cutting blade 116 and toward a generally planar radially inner portion 174 of the leading surface. The radially outer, arcuate portion 172 extends from a radially outer end thereof in a direction substantially tangential to the radially inner surface of the annular cutting blade 116. Moreover, the radially outer, arcuate portion 172 curves radially inwardly between the radially outer and radially inner ends thereof. The inner portion 174 of the leading surface 170 extends radially inward relative to the axis of rotation A in a direction generally transverse to the perimeter of the annular tissue-removing head 110. The inner portion 174 of the leading surface 170 intersects a trailing surface, generally indicated at 176, of the inner shearing member 126. An axial end surface, generally indicated at 178, intersects the leading surface 170 and trailing surface 176 at leading and trailing edges 180, 182, respectively, and extends radially outward toward the cutting blade 116.

Figure 10:
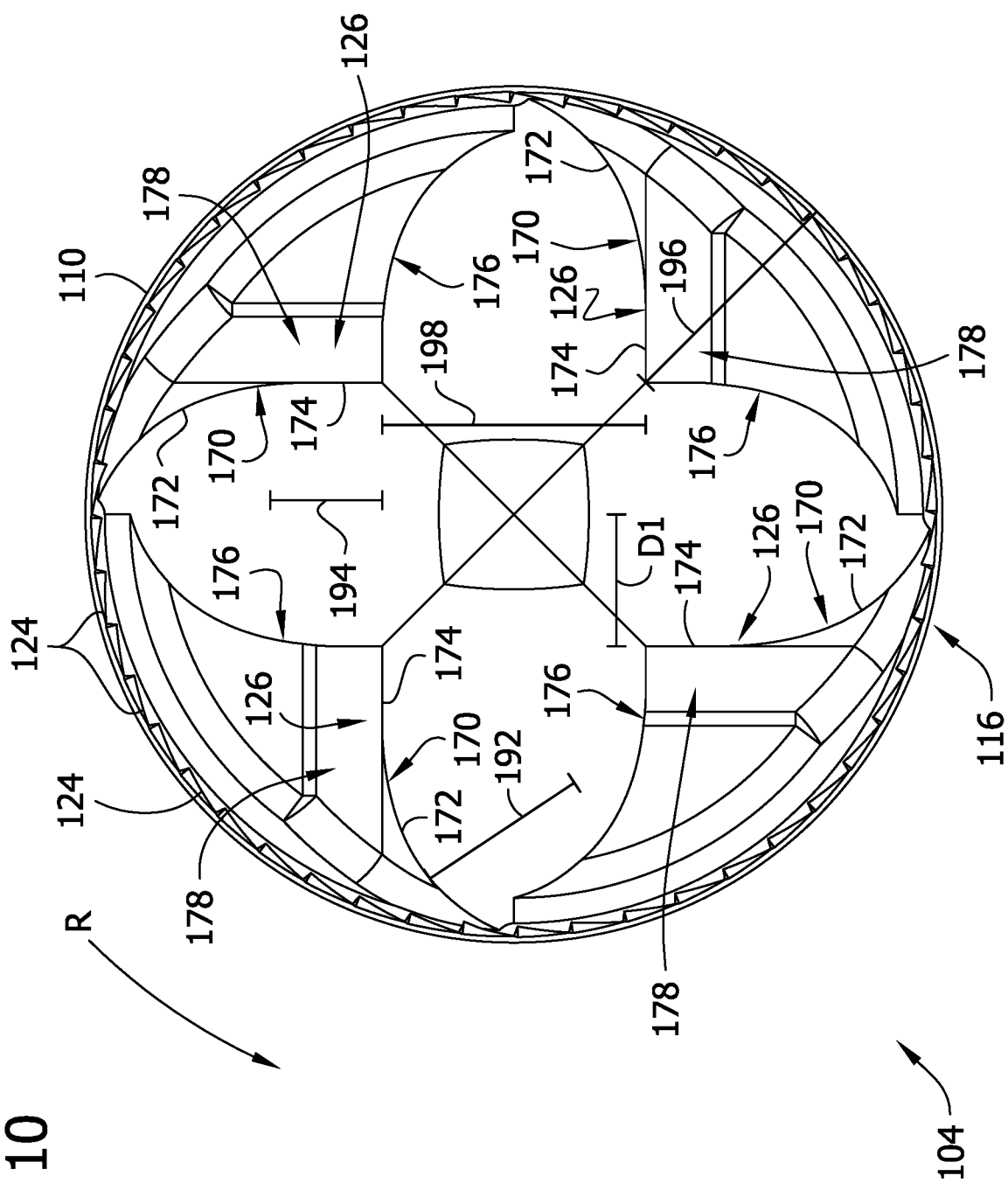
FIG. 10 is top plan view of the tissue-removing element of FIG. 4.

In the illustrated embodiment, the arcuate portion 172 of the leading surface 170 of each inner shearing member 126 is configured to shear tissue radially inward with respect to the tissue-removing element 4. The trailing portion 174, which acts as the impact surface of the inner shearing member 126, is configured to impact tissue at an obtuse angle to further shear the tissue radially inwardly as the tissue-removing element 4 rotates in the cutting direction R. Referring to FIG. 10, the arcuate portion 172 has a radius of curvature 192, and the trailing portion 174 has a length 194. The dimensions for the radius of curvature 192 and the length 194 affect the shearing action of the arcuate portion 172 and the impacting action of the trailing portion 174 and are limited by the available space for the inner shearing member 126. In the illustrated embodiment, the radius of curvature 192 may be about 0.0085 in. In one or more embodiments, the radius of curvature 192 of the arcuate portion 72 of the inner shearing member 126 may be from about 1% to about 50% of the radius of the tissue-removing blade 116. Likewise, in one or more embodiments, the length 194 of the impact surface of an inner shearing member (e.g., the trailing portion 74 of the radially inner surface 46) may be from about 1% to about 75% of the radius of the outer tissue-removing blade 116.

Referring further to FIG. 10, in the illustrated embodiment, the four inner shearing members 126 are formed in a crosscut pattern (i.e., the cup-shaped surfaces defining the recess 118 are cross-shaped). The crosscut pattern enables the inner shearing members 126 to be machined relatively easily using a single cutting implement. The crosscut can have a fixed or variable axial depth without departing from the scope of the invention. A crosscut width 198 measures the distance between the trailing surface 176 of one inner shearing member 126 and the impact surface (i.e., the radially inner portion 174 of the radially inner surface 170) of the adjacent, trailing inner shearing member. In the illustrated embodiment, adjacent impact and trailing surfaces 174, 176 are oriented substantially parallel to one another. The crosscut width 198 is preferably chosen to optimize the angle of impact of the inner shearing member 126 and to use a relatively large cutting implement.

If the impact surface 174 were in line with a radius of the tissue-removing head 110, the inner shearing member would impact hard tissue at an impact angle perpendicular to the impact surface, which may cause braking of the rotation of the tissue-removing element 104 and reduce tissue-removal efficiency. In the illustrated embodiment, the plane of the impact surface 174 of each inner shearing member 126 is offset a distance D1 (e.g., about 0.010 inches) from the axis of rotation A in a direction perpendicular to the plane. In one or more preferred embodiments, the impact surface of an inner shearing member is offset from the axis of rotation in a direction perpendicular to the plane a distance D1 that is from about 10% to about 70% of the outer radius of the tissue-removing head 110. As a result, the impact surface 174 of each inner shearing member 126 impacts hard tissue at an obtuse impact angle. This reduces the tendency of impacts between one of the inner shearing members 126 and hard tissue to cause braking of the rotating tissue-removing element 104, which enables a user to impart less axial force on the catheter 2 to advance the tissue-removing element through the body lumen. In addition, it enables impacts between the tissue and the impact surface 174 to shear the tissue away from the body lumen wall.

Referring still to FIG. 10, each inner shearing member 126 has a radial length 196 that is measured as the distance between the radially outer surface of the tissue-removing head 110 and the radially innermost point of the inner shearing member 126 along an imaginary line (i.e., a radius of the cutting blade 116 and tissue-removing head 110) that passes through both the axis of rotation A and the innermost point of the inner shearing member 126 in a plane parallel to the cutting plane P. To maximize the capability of the inner shearing member 126 to impact tissue at any radial position in the body lumen, the radial length 196 may be equal to the radius of the tissue-removing head 22. However, to facilitate the crosscut pattern by which the inner shearing members 126 are manufactured, the inner shearing member radial length 196 is preferably less than the radius of the tissue-removing head 110. In one or more embodiments, the inner shearing member radial length 196 may be from about 10% to about 80% of the radius of the tissue-removing head 110. In the illustrated embodiment, the inner shearing member radial length 196 may be about 0.018 in. In one or more embodiments, the inner shearing member radial length 196 is sized so that, as the cutting element 104 rotates in the deployed position, the inner shearing member spans the entire distance between the cutter opening 6 and the cutting blade 116. This arrangement maximizes the engagement between the inner sharing member 126 and the tissue. Alternatively, the breaker radial length 196 can be sized so that, as the cutting element 104 rotates in the deployed position, the inner shearing member 126 spans only a radially outer portion of the distance between the cutter opening 6 and the cutting blade 116. This arrangement allows the cup-shaped portion of the cutting head 110 to redirect cut tissue toward the tissue chamber 12.

Figure 11:
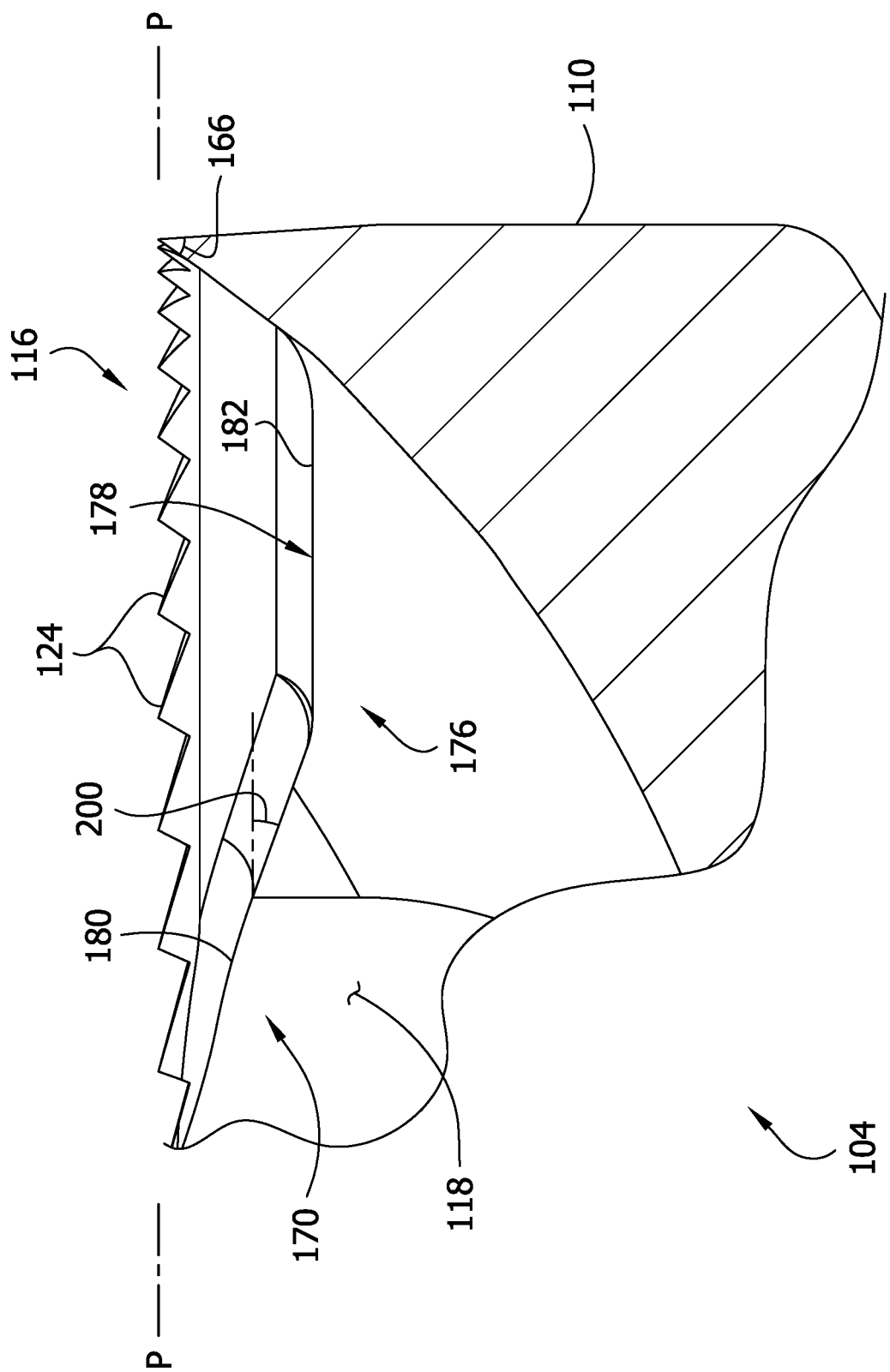
FIG. 11 is another fragmentary section of the tissue-removing element of FIG. 4.

As shown in FIG. 11, a leading portion of the axial end surface 178 is oriented at a relief angle 200 relative the impact surface 174. In one or more preferred embodiments, the relief angle 200 is between about 1° and about 75°. In the illustrated embodiment, the relief angle 200 is about 20°.

In an exemplary method of making the tissue-removing element 104, the tissue-removing element can be formed by removing material from a blank comprising a single piece of material using one or more cutting implements. In one or more embodiments, a blank comprises a generally cylindrical body of material with opposite first and second axial ends and an axis extending between the axial ends. In certain embodiments, only an axial end portion at the first axial end of the blank, which corresponds with the tissue-removing head 110 of the tissue-removing element 104, is cylindrical. Thus, the blank can be preformed to have the shape of the stem 114 of the tissue-removing element 104 or can be machined to form the shape of the stem as part of a method of making a tissue-removing element without departing from the scope of the invention.

In one method of making a tissue-removing element 104, a cutting implement, such as a milling cutter of a multi-axis mill or Swiss machine, removes material from the blank to form the cutting teeth 124 and likewise removes material from the blank to form the inner shearing member 126. A ninety-degree cutting implement preferably removes material from the blank to form a leading surface 142 and axial end surface 150 of each cutting tooth simultaneously. To form the leading and trailing surfaces 170, 176 of the inner shearing members 126, a cutting implement is preferably moved along a desired depth profile relative to the tissue-removing head 110 and passed along a cross-shaped cutting path.

An exemplary method of using the catheter 2 to remove tissue from a body lumen will now be described. A user inserts the catheter 2 into the body lumen (such as by using a guidewire), positions the tissue-removing element 104 in the deployed position, and rotates the tissue-removing element in the cutting direction R as the catheter advances axially through the lumen. The cutting blade 116 engages tissue (e.g., plaque) in the body lumen as the tissue-removing element 104 rotates about its rotation axis A and advances axially through the lumen. The cutting teeth 124 engage the tissue first, before the corresponding inner shearing member 126. As the tissue-removing element 104 rotates in the cutting direction R, the leading surface 142 of a cutting tooth 124 slices into the tissue adjacent the body lumen wall. The radially inner surface 146 of the cutting tooth 124 shears the tissue radially inward, toward the axis of rotation A.

With continued axial advancement of the catheter 2 and rotation of the tissue-removing element 104, the adjacent, trailing cutting teeth 124 cut into the tissue as described above. Tissue that is positioned radially inward of the depression created by the cutting tooth 124 rides along the radially inner surface cutting blade 116. When the outer arcuate portion 172 of the leading surface 170 of the inner shearing member 126 engages the tissue, it shears the tissue radially inward. Depending on the material properties of the tissue, the tissue might fracture upon engaging the arcuate portion 172 or curl radially inwardly in response to the shearing. The inner impact portion 174 of the leading surface 170 impacts any tissue located at a sufficiently radially inward position for engagement therewith at an obtuse angle, which causes further shearing of the tissue. Preferably, the impact between the impact surface 174 and the tissue imparts a stress on the tissue that causes the tissue to fracture or otherwise break away from the body lumen for removal therefrom. With continued axial advancement of the catheter 2 and rotation of the tissue-removing element 104, the adjacent trailing inner shearing member 26 subsequently engages the tissue in much the same way. The rotation of the tissue-removing element 104 in the cutting direction R preferably directs fractured tissue distally of the tissue-removing element and into the tissue collection chamber 12.

Figure 12:
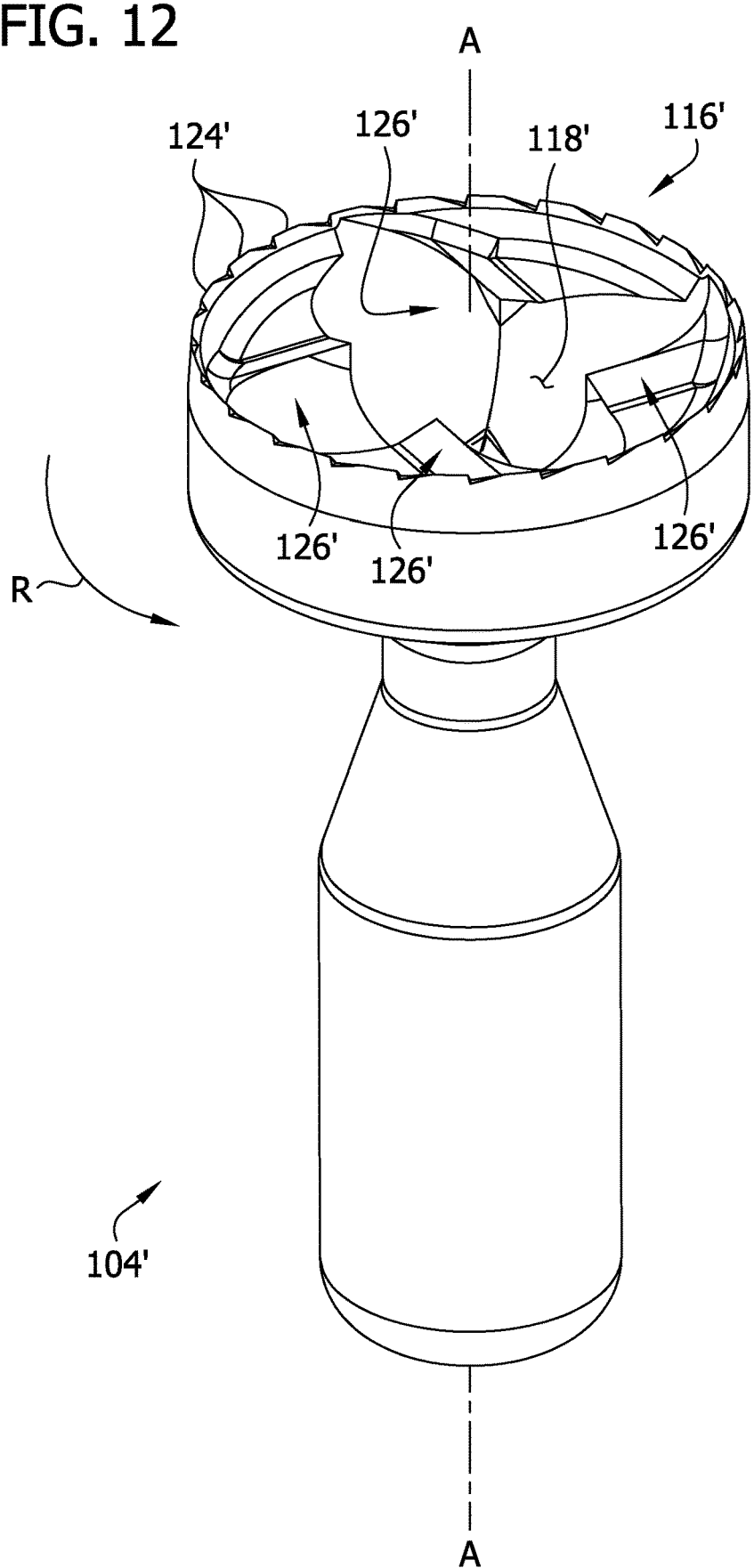
FIG. 12 is a perspective of another tissue-removing element.
Figure 13:
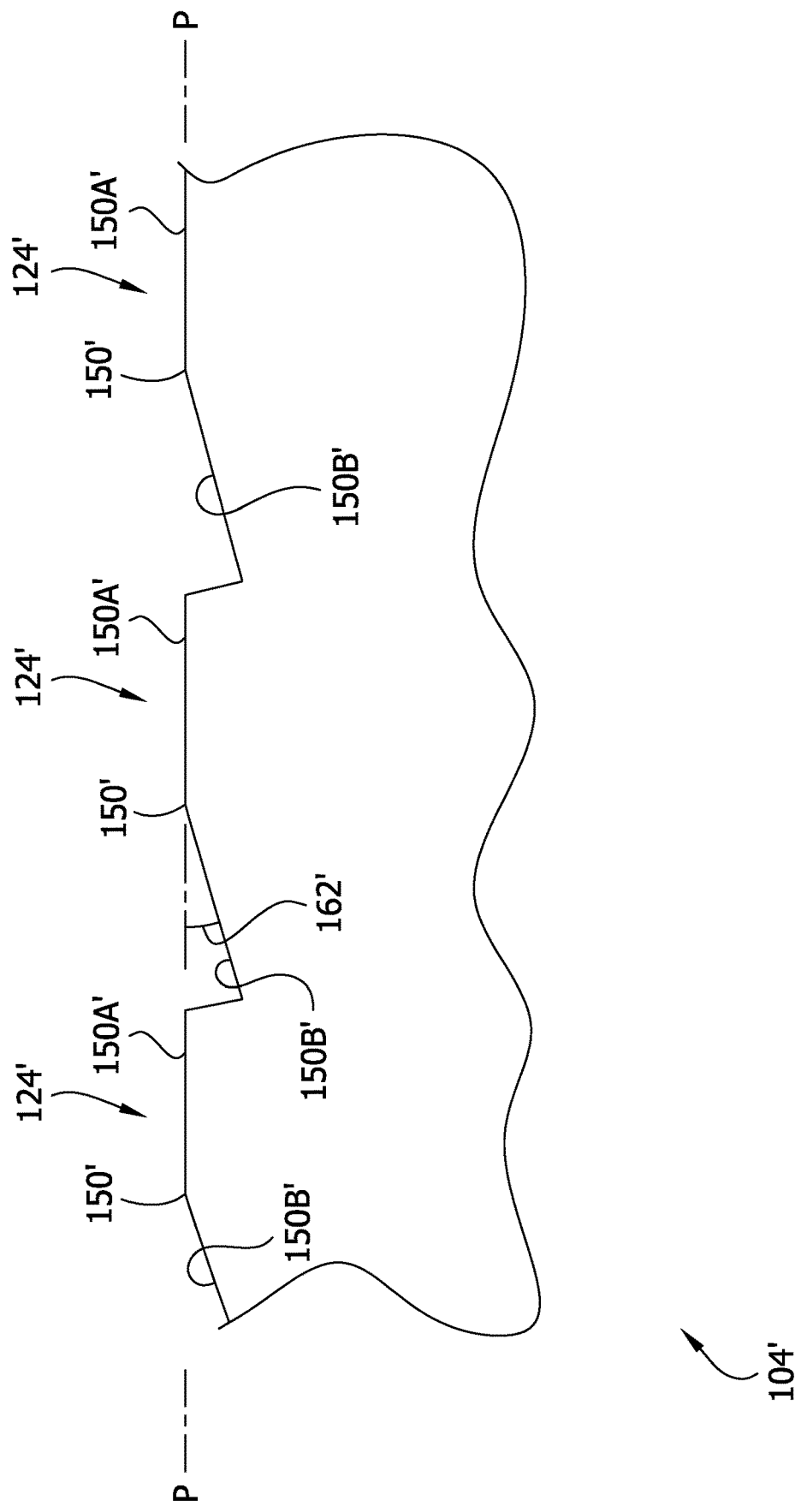
FIG. 13 is a fragmentary elevation of the tissue-removing element of FIG. 12.

Referring to FIGS. 12-13, another embodiment of a tissue-removing element is generally indicated at reference numeral 104'. The present tissue-removing element 104' is substantially similar to the tissue-removing element 104, except for the differences that are, in part, apparent and, in part, pointed out hereinafter. Features of the tissue-removing element 104' are given the reference number of corresponding features of the tissue-removing element 104, followed by a prime symbol. Like the tissue-removing element 104, the distal end of the tissue-removing element 104' includes an annular tissue-removing blade generally indicated at 116' comprising cutting teeth 124' that circumscribe a recess 118' that is cross-cut to have four inner shearing members 126'. The tissue-removing blade 116' comprises fewer teeth (e.g., 24 teeth) than the tissue-removing blade 116 (e.g., 48 teeth). Referring to FIG. 13, axial end surfaces 150' of the cutting teeth 124' are truncated at truncated portions 150A' to lessen the effective relief of the teeth 124'. The truncated portion 150A' of the axial end surface 150' of each cutting tooth 124' lies in the cutting plane P, which provides an intermittent smooth edge for engaging tissue as the tissue-removing element 104' rotates in the cutting direction R (FIG. 12) about its axis of rotation A inside a body lumen. A trailing portion 150б' has a 15° relief angle 162'. In other embodiments it is contemplated that the truncated portion 150A could also be slightly relieved so only the tips of the teeth are in the cutting plane.

Figure 14:
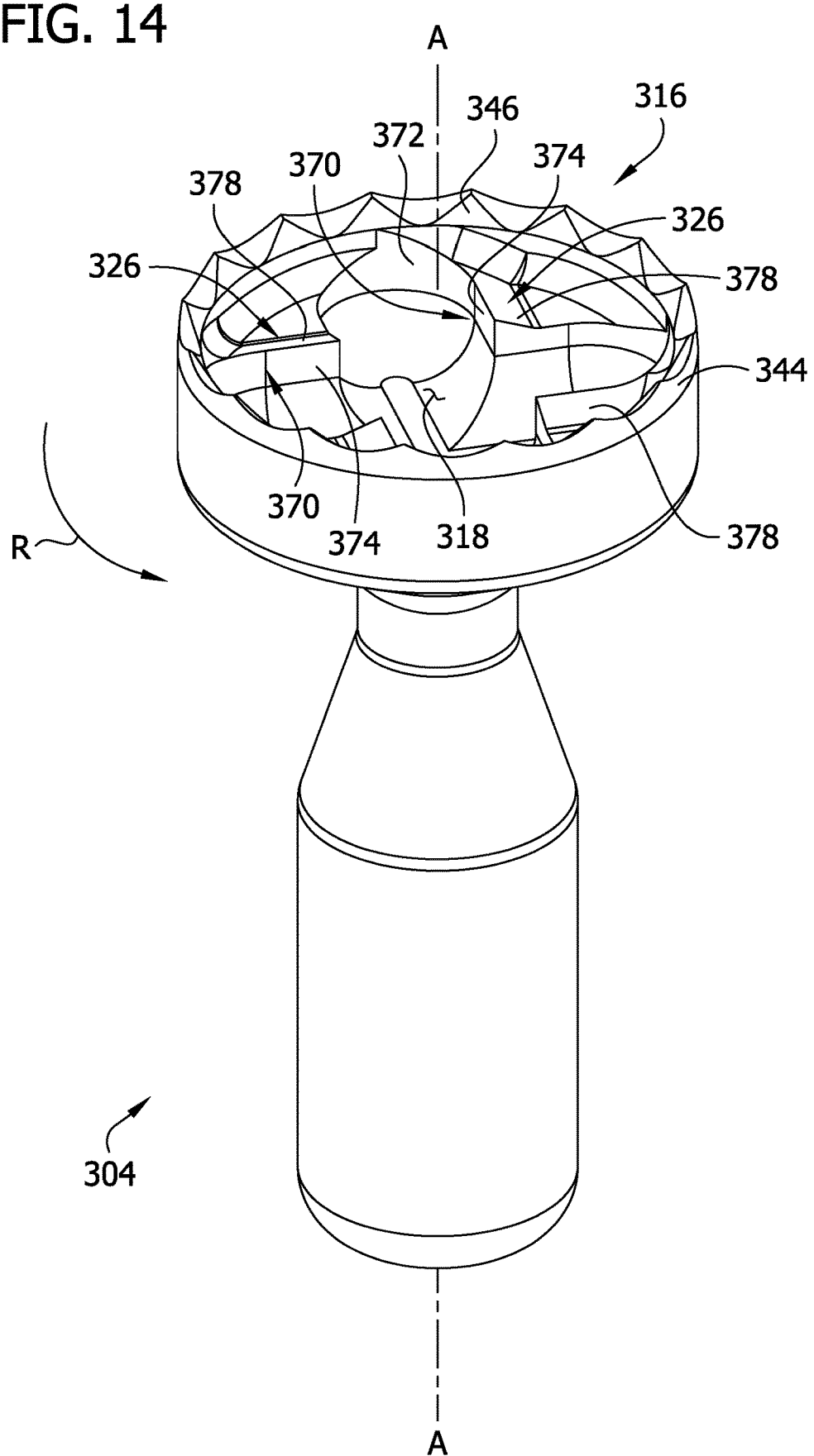
FIG. 14 is a perspective of another tissue-removing element.

Referring to FIG. 14, another embodiment of a tissue-removing element suitable for use with the catheter 2 is generally indicated at reference number 304. The tissue-removing element 304 has a body with proximal and distal axial ends. At the distal end of the body, the tissue-removing element 304 includes a serrated annular tissue-removing blade 316. In addition, the distal end of the tissue-removing element 304 includes four inner shearing members 326 (which are substantially similar to the inner shearing members 126 of the tissue-removing element 104). The annular tissue-removing blade 316 has a radially outer surface 344 and a radially inner surface 346 that extend axially in the distal direction from the distal end of the tissue-removing element 304. The radially inner surface 346 of the annular tissue-removing blade 316 slopes radially outwardly as the radially inner surface extends axially in the distal direction. The illustrated tissue-removing element 304 is a one-piece body. Thus, the serrated tissue-removing blade 316, the inner shearing members 326, and the tissue-removing element body are all formed from one piece of material, preferably by removing material from a blank using a conventional machining process such as milling or Swiss machining.

The annular tissue-removing blade 316 circumscribes a recess 318 at the distal end of the tissue-removing element 304. The recess 318 defines four inner shearing members 326. Each inner shearing member 326 has a leading surface, generally indicated at 370, that includes a radially outer, arcuate portion 372 and a radially inward planar portion 374. The tissue-removing element 304 is configured to operably connect to the drive shaft 20 of the catheter 2 to rotate about an axis of rotation A in a cutting direction R. The impact surfaces 374 of the inner shearing members 326 are arranged to impact tissue as the tissue-removing element 304 rotates in the cutting direction R. Each inner shearing member 326 has an axial end surface 378. In the illustrated embodiment, a leading portion of each axial end surface 378 is oriented at a relief angle of about 20° relative the cutting plane of the tissue-removing element. However, it will be understood that other inner shearing member relief angles can also be used without departing from the scope of the invention.

Figure 15:
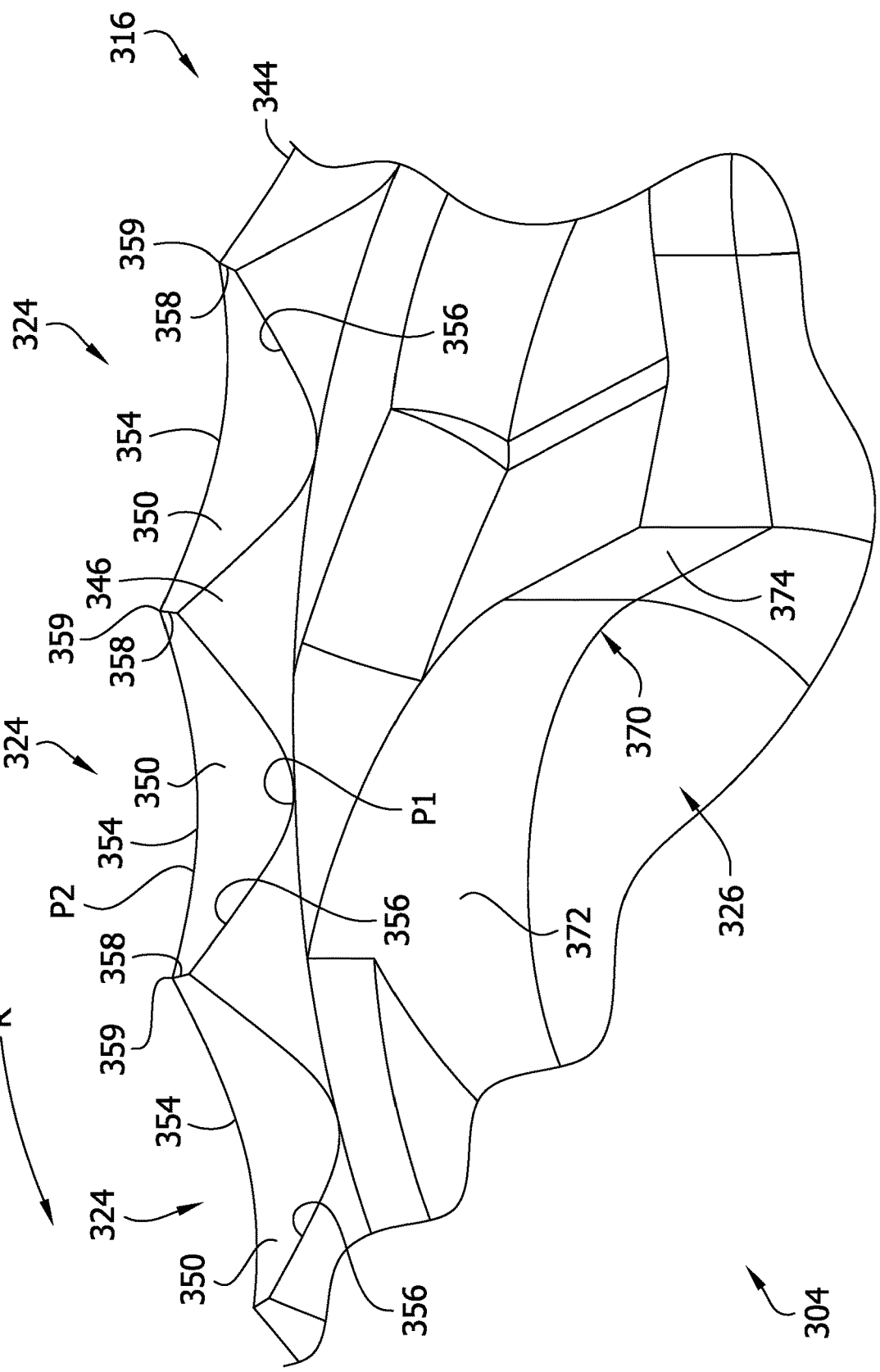
FIG. 15 is a fragmentary perspective of the tissue-removing element of FIG. 14.

Referring to FIG. 15, the annular tissue-removing blade 316 of the illustrated tissue-removing element 304 includes 16 serrations, generally indicated at reference number 324. Although the illustrated embodiment includes 16 serrations, it will be understood that other numbers of serrations may also be used without departing from the scope of the invention. Each serration 324 has an axial end surface 350 that intersects the radially outer surface 344 of the tissue-removing blade 316 at a radially outer edge 354 and the radially inner surface 346 of the tissue-removing blade at a radially inner edge 356. The radially outer edge 354 is curved proximally (i.e., has a concave shape). The radially inner edge 356 of each serration 324 is also curved proximally (i.e., has a concave shape). For each serration 324, a turning point P1 along the radially inner edge 356 is located proximal of a turning point P2 along the the radially outer edge 354 such that the axial end surface 350 of each serration is a generally concave surface that faces radially inwardly and distally and slopes proximally and radially inwardly between the radially outer edge and radially inner edge. Each serration 324 has leading and trailing peaks 358. The trailing peak 358 of one serration 324 is also the leading peak of the adjacent trailing serration. The peaks slope radially inwardly and proximally away from a penetration tip 359 at the radially outer edge 354.

Referring to FIGS. 14 and 15, in use as the tissue-removing element 304 rotates about the axis of rotation A in the cutting direction R and translates axially through a body lumen, the serrated tissue-removing blade 316 engages tissue in the body lumen. The leading penetration tip 359 of a serration 324 pierces the tissue, and the radially outer edge 354 slices through it as the tissue-removing element 304 rotates in the cutting direction R. At the same time, as the tissue-removing element 304 advances axially through the lumen, the axial end surface 350 of the serration 324 engages the tissue and shears it radially inward toward the recess 318. The arcuate portion 372 of the inner shearing member 326 engages the tissue in the recess and shears it further radially inward toward the axis of rotation A. The planar portion 374 impacts the tissue at an obtuse angle, causing it to fracture away from the luminal wall.

In one or more suitable methods of manufacturing the tissue-removing element 304 a cutting implement of a milling machine removes material from a one-piece blank using conventional machining techniques. The cutting implement is positioned at an angle relative to the axis of rotation A and travels along a cutting path while oriented at the angle to form one of the serrations 324. An adjacent serration 324 can be formed by rotating the tissue-removing element 304 about its axis of rotation relative to the cutting implement (e.g., one-sixteenth of one complete rotation) and driving the cutting implement along the cutting path a second time. These steps can be repeated to sequentially form each of the serrations 324.

Figure 16:
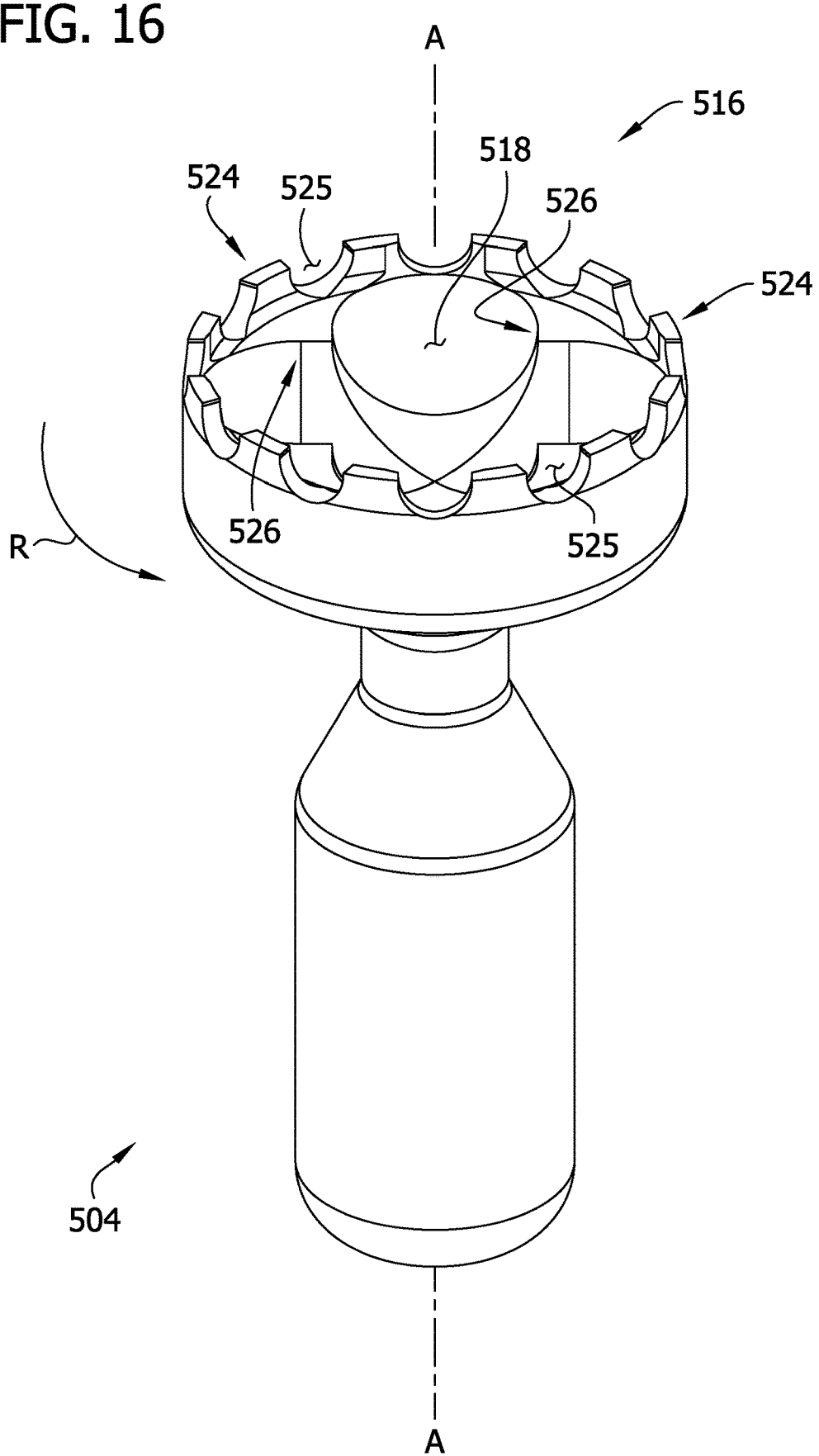
FIG. 16 is a perspective of another tissue-removing element.

Referring to FIG. 16, another embodiment of a tissue-removing element suitable for use with the catheter 2 is generally indicated at reference number 504. Like the tissue-removing element 304, the tissue-removing element 504 is configured for operative connection with the drive shaft 20 of the catheter 2 for rotation about an axis of rotation A in a cutting direction R. One skilled in the art will appreciate that the tissue-removing element 504 is formed symmetrically about the axis of rotation A so that the tissue-removing element can also be rotated in a direction opposite the cutting direction R and have the same tissue-removal characteristics as when the tissue-removing element is rotated in the cutting direction. The tissue-removing element 504 has a body with proximal and distal axial ends. At the distal end of the body, the tissue-removing element 504 includes an annular tissue-removing blade 516 including a plurality cutting teeth 524. In addition, the distal end of the tissue-removing element body includes four inner shearing members 526. The illustrated tissue-removing element 504 is a one-piece body. Thus, the crenellated tissue-removing blade 516, the inner shearing members 526, and the tissue-removing element body are all formed from one-piece of material, preferably by removing material from a blank using a conventional machining process such as milling or Swiss machining.

Figure 17:
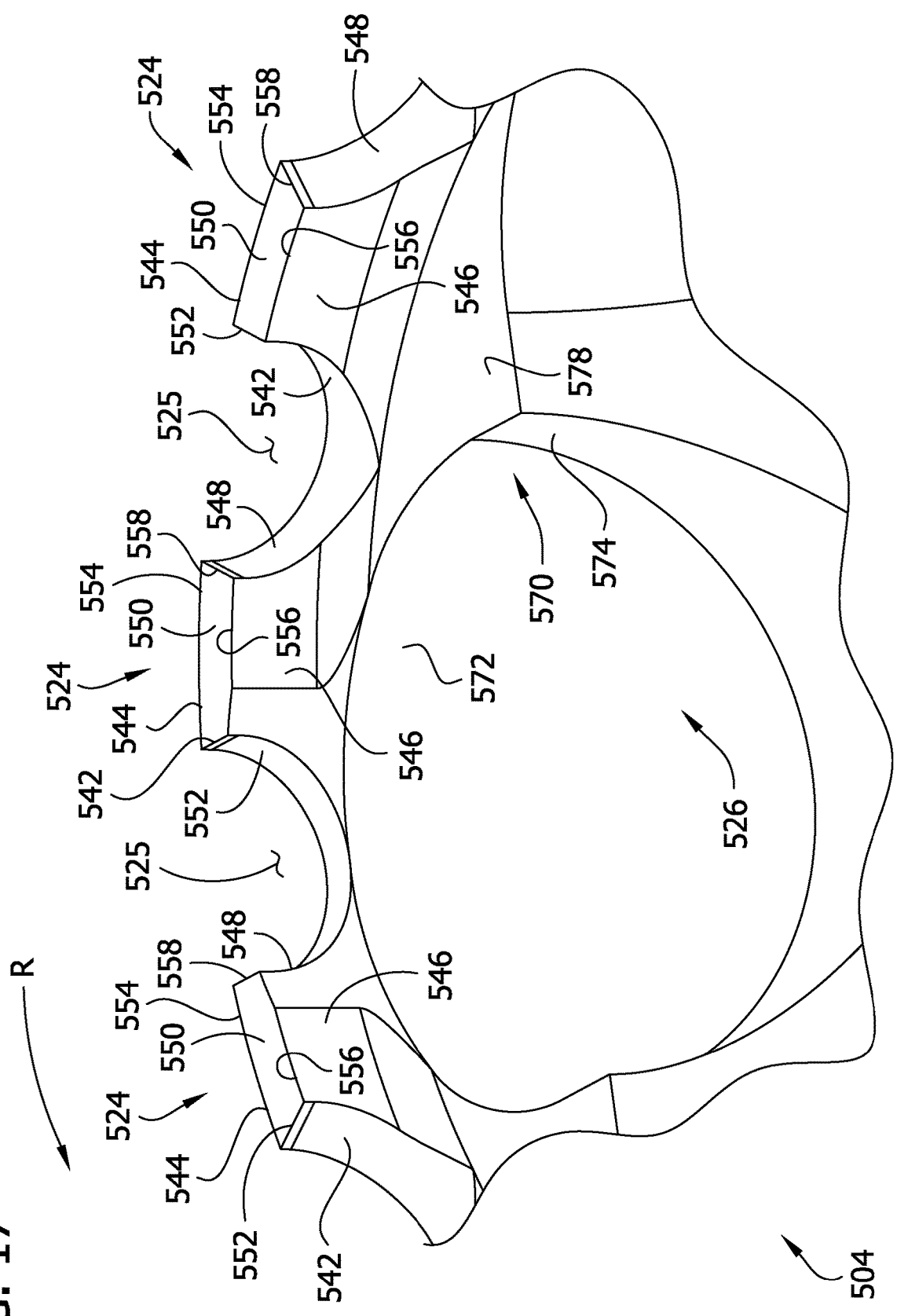
FIG. 17 is a fragmentary perspective of the tissue-removing element of FIG. 16.

Referring to FIG. 17, the tissue-removing blade 516 comprises a plurality of merlon-shaped cutting teeth 524 spaced radially outward of the axis of rotation A and angularly around the tissue-removing blade 516 and a plurality of crenel-shaped gaps 525 interleaved between the plurality of cutting teeth. Each tooth 524 has a leading surface 542, radially outer surface 544, radially inner surface 546, and trailing surface 548. For each tooth 524, the radially inner surface 546 is oriented substantially parallel to the radially outer surface 544 so that the tooth has a generally rectangular cross-sectional shape, which cuts a generally rectangular kerf in the tissue (particularly in hard tissue). Although the radially outer and inner surfaces 544, 546 are substantially parallel to one another in the illustrated embodiment, in other embodiments it is contemplated that the inner and outer surfaces of the cutting teeth could be oriented at an angle relative to one another. For example, in certain embodiments, the outer surface may be angled inward to provide additional clearance when moving the tissue-removing element between the stored and deployed positions. An axial surface 550 intersects the radially outer surface 544, radially inner surface 546 and trailing surface 548 at leading edge 552, radially outer edge 554, radially inner edge 556, and trailing edge 558. The axial end surface 550 of each tooth 524 is oriented substantially parallel to the cutting plane. However, in other embodiments, it is contemplated that the axial end surface of a tooth could be angled with respect to the cutting plane without departing from the scope of the invention.

Figure 18:
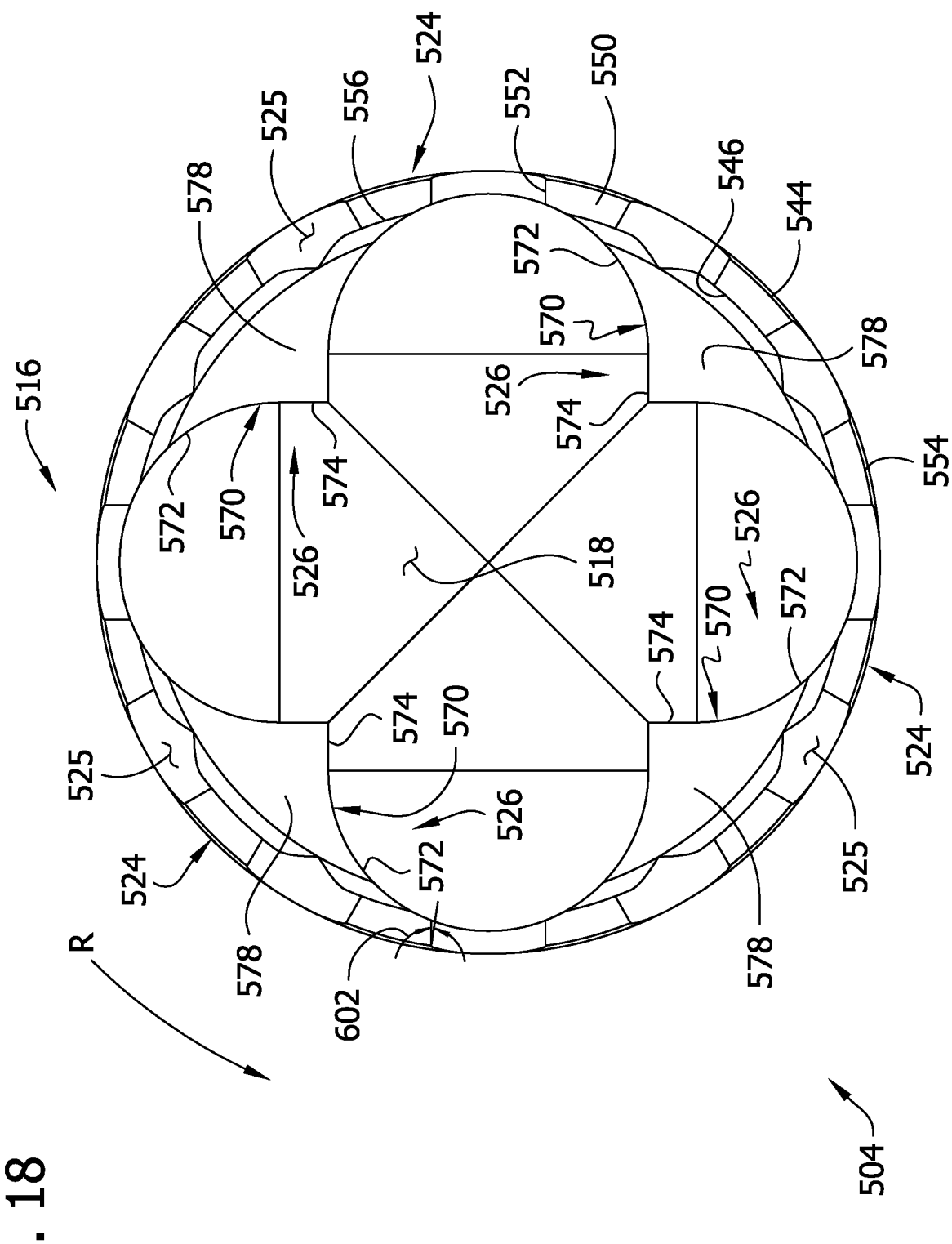
FIG. 18 is a top plan view of the tissue-removing element of FIG. 16.

The trailing surface 558 of a leading tooth 524 and the leading surface 542 of an adjacent, trailing tooth define a gap 525, which in the illustrated embodiment is U-shaped. In the illustrated embodiment, the proximal surface of the gap 525 is curved. It will be understood that, in other embodiments, the proximal surface of the gap could have a different radius than in the illustrated embodiment or be non-curved such that the gap is substantially rectangular. As shown in FIG. 18, the leading edge 552 of each tooth 524 is oriented at a positive fleam angle 602. When the tissue-removing element 504 is viewed from the distal axial end as shown in FIG. 18, the fleam angle 602 is the angle between the leading edge 552 and a line perpendicular to a line tangent to the perimeter of the annular cutting blade 516 at the leading edge. Because of the fleam angle 602, as the tissue-removing element 504, rotates about its axis of rotation A, a radially outer portion of the leading surface 542 of a tooth 524 engages tissue before a radially inner portion thereof. Thus, the leading surface 542 is arranged to shear tissue radially inwardly toward the axis of rotation A as the tissue-removing element 504 rotates in the cutting direction R.

Referring to FIG. 18, the annular tissue-removing blade 516 circumscribes a recess 518 at the distal end of the tissue-removing element 504. A cross-cut pattern is formed in the recess 518 so that the recess defines four inner shearing members 526. Each inner shearing member 526 has a leading surface 570 that includes a radially outer, arcuate portion 572 and a radially inward planar portion 574. The leading surfaces 570 of the inner shearing members 526 are arranged to impact and shear tissue radially inwardly as the tissue-removing element 504 rotates in the cutting direction R. Each inner shearing member 526 has an axial end surface 578. In the illustrated embodiment, the axial end surface 578 is not relieved relative the cutting plane (e.g., the axial end surface 578 is oriented substantially parallel to the cutting plane). However, it will be understood that the axial end surface 578 of the inner shearing member 526 could be formed at a relief angle relative the cutting plane without departing from the scope of the invention.

Figure 19:
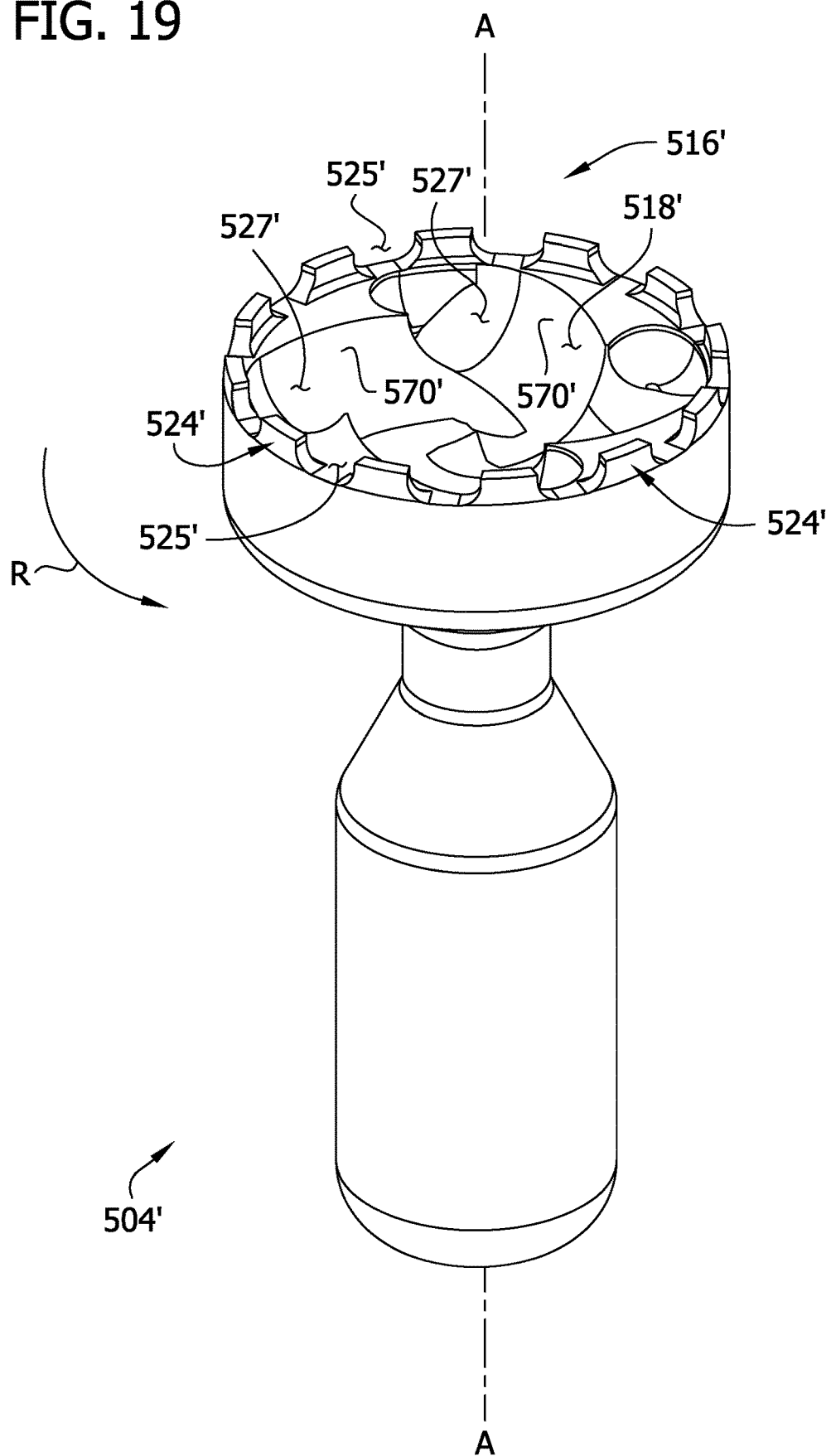
FIG. 19 is a perspective of another tissue-removing element.
Figure 20:
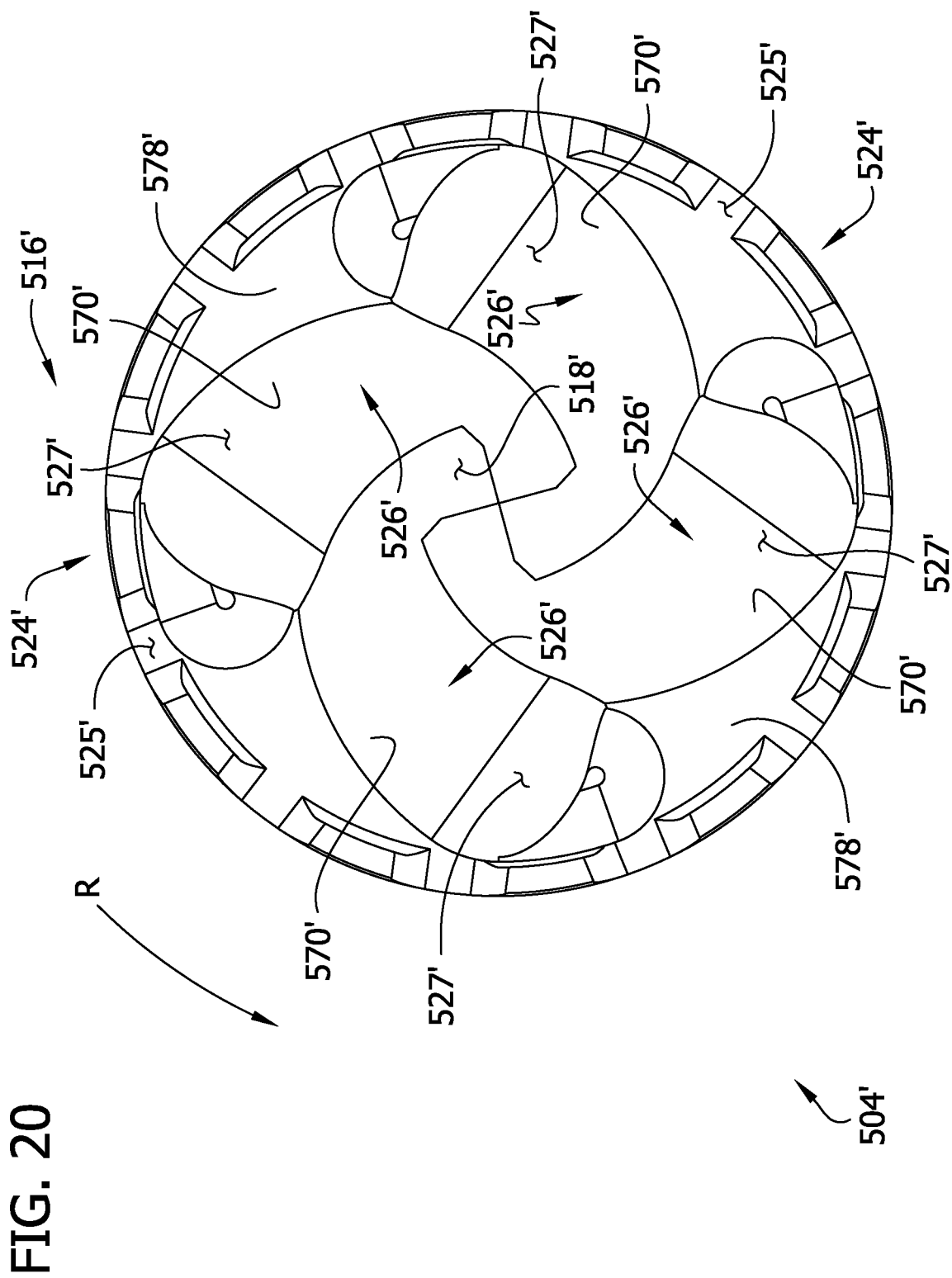
FIG. 20 a top plan view of the tissue-removing element of FIG. 19.

Referring to FIGS. 19-20, a tissue-removing element 504' is substantially similar to the tissue-removing element 504, except for the differences that are, in part, apparent and, in part, pointed out hereinafter. Features of the tissue-removing element 504' are given the reference number of corresponding features of the tissue-removing element 504, followed by a prime symbol. Like the tissue-removing element 504, the tissue-removing element 504' includes a crenellated tissue-removing blade 516' made up of alternating merlon-shaped cutting teeth 524' and crenel-shaped gaps 525'. The tissue-removing blade 516' circumscribes a recess 518' that is shaped to define four inner shearing members 526'. Whereas the recess 518 of the tissue-removing element 504 is machined in a crosscut pattern to create the inner shearing members 526, inner shearing members 526' are formed into the recess 518' with four grooves 527' that extend radially outward from the center of the recess and curve angularly toward the leading direction (relative the cutting direction R) as they extend radially outward. The grooves 527' define leading surfaces 570' that are curved along their entire radial length. Like the inner shearing members 526, the inner shearing members 526' have axial end surfaces 578' that are not relieved relative the cutting plane. It will be understood that the curved construction of the shearing members 526' can also be used with other embodiments of tissue-removing elements.

Figure 21:
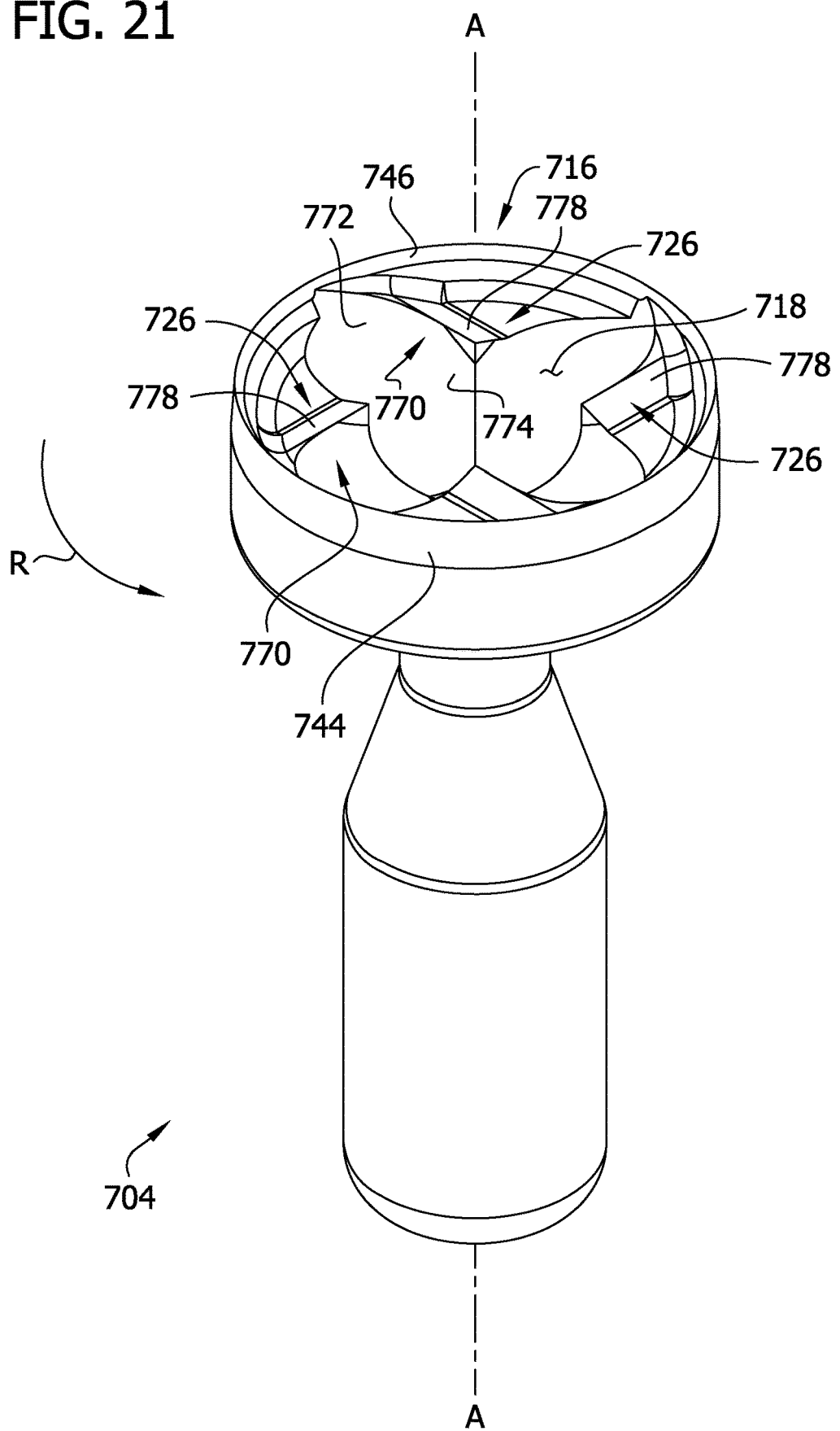
FIG. 21 is a perspective of another tissue-removing element.

Referring to FIG. 21, another embodiment of a tissue-removing element suitable for use with the catheter 2 is generally indicated at reference number 704. The tissue-removing element 704 has a body configured for operative connection to the drive shaft 20 of the catheter 2 for rotation about an axis of rotation A in the cutting direction R. Unlike the tissue-removing elements 104, 304, 504, the tissue-removing element 704 has a continuous tissue-removing blade, generally indicated at 716. The tissue-removing blade 716 extends axially in the distal direction from the distal end of the tissue-removing element 704 and circumscribes a recess 718. A cross-cut pattern is formed in the recess to define four inner shearing members 726. The illustrated tissue-removing element 704 is a one-piece body. Thus, the tissue-removing blade 716, inner shearing members 726, and tissue-removing element body are all formed from one piece of material, preferably by removing material from a blank using a conventional machining process such as milling or Swiss machining.

The tissue-removing blade 716 has a continuous, annular radially outer surface 744 and a continuous, annular radially inner surface 746. The radially inner surface 746 slopes radially outwardly as the tissue-removing blade 716 extends axially in the distal direction. The radially outer surface of the tissue-removing blade 716 is angled slightly radially inward to provide clearance for moving the tissue-removing element 704 between the stored and deployed positions. Thus the tissue-removing blade 716 has a wedge-shaped cross-sectional shape. Each of the inner shearing members 726 has a leading surface 770 comprising a radially outer, arcuate portion 772 and a radially inner substantially planar portion 774. In addition, each inner shearing member 726 has an axial end surface 778. A leading portion of each axial end surface 778 is oriented at a relief angle relative a cutting plane of the tissue-removing element 704. As will be appreciated, the distal end of the continuous annular tissue-removing blade 716 is positioned in the cutting plane of the tissue-removing element 704.

As the tissue-removing element 704 rotates in the cutting direction R in a body lumen, the annular tissue-removing blade 716 is configured to slice through tissue therein. As the tissue-removing element 704 advances axially through the lumen, the radially inner surface 746 of the tissue-removing blade 716 shears the tissue radially inward toward the axis of rotation A. The radially outer, arcuate portions 772 of the inner shearing members 726 shear the tissue further radially inward as the tissue-removing element rotates in the cutting direction R, and the substantially planar portions 774 impact the tissue at an obtuse angle to break it away from the luminal wall.

Figure 22:
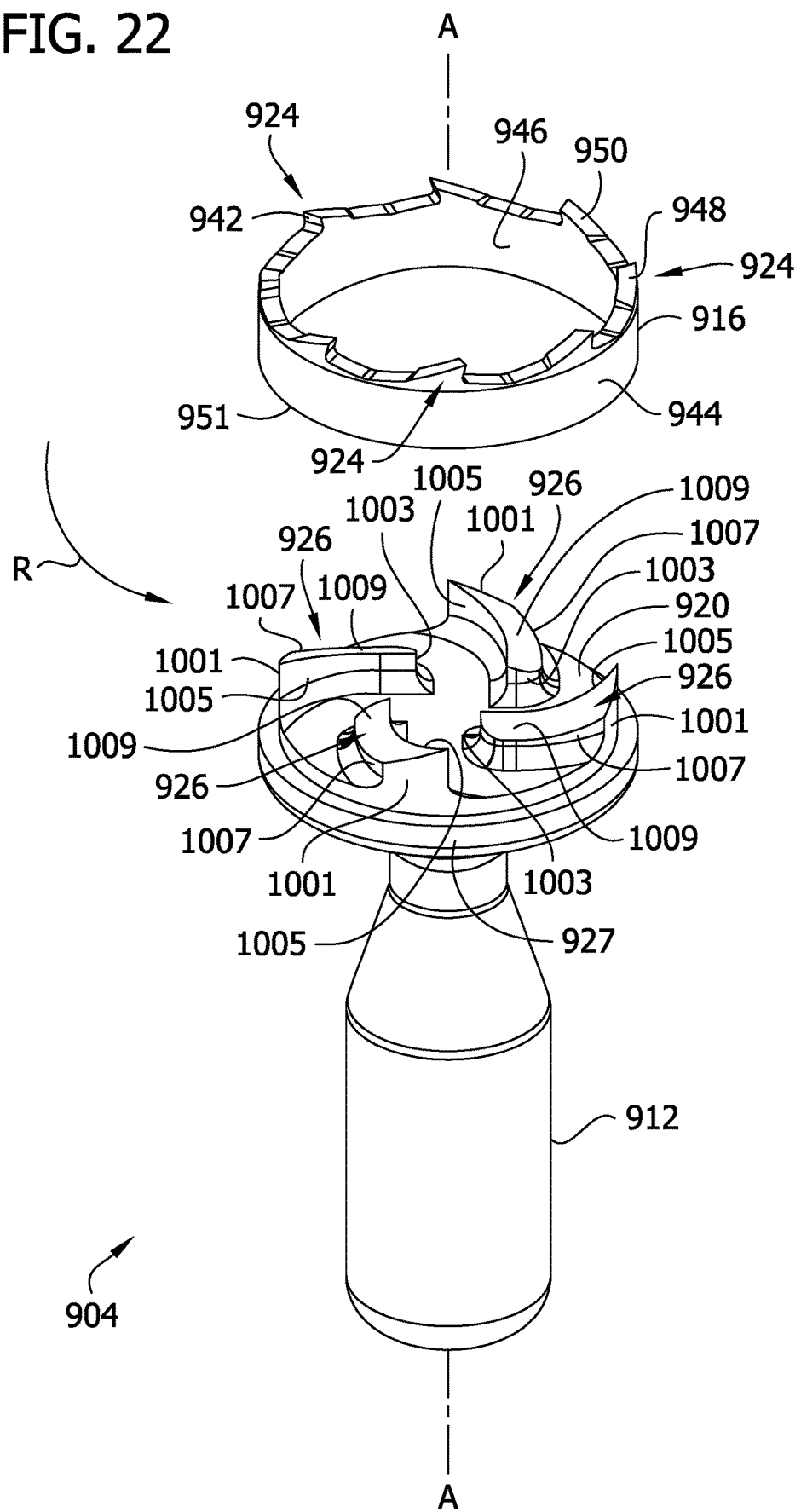
FIG. 22 is an exploded perspective of another tissue-removing element.

Referring to FIG. 22, in certain embodiments, a tissue-removing element 904 can include a tissue-removing element body member 912 and an annular tissue-removing blade member 916 that are made separately from one another. The tissue-removing element 904 is configured for operative connection with the drive shaft 20 of the catheter 2 for rotation about an axis of rotation A in a cutting direction R. In the illustrated embodiment, the body member 912 has a distal end and a proximal end. The distal end includes a substantially planar axial end surface 920. Four inner shearing members 926 spaced angularly about the axis of rotation A extend axially in the distal direction from the axial end surface 920 of the distal end of the body member 912. Each inner shearing member 926 includes a radially outer surface 1001, radially inner surface 1003, leading surface 1005, trailing surface 1007, and axial end surface 1009. In use, the tissue-removing element body 912 is configured to rotate about the axis of rotation A in a cutting direction R. The leading surface 1005 of each inner shearing member 926 leads the trailing surface 1007 as the tissue-removing element body member 912 rotates in the cutting direction R. The distal end of the body member 912 also includes an annular shoulder 927 that encircles the inner shearing members 926 and defines a seat for securing the annular tissue-removing blade 916 to the body. The annular shoulder 927 includes a radially outwardly facing portion and an axially distally facing portion The radially outwardly facing portion of the annular shoulder 927 forms a continuous annular surface with the radially outer surfaces 1001 of the inner shearing members 926.

The annular tissue-removing blade member 916 is has a radially outer surface 944, a radially inner surface 946, a distal end 950, and a proximal end 951. In the illustrated embodiment, the radially outer surface 944 and the radially inner surface 946 are parallel annular surfaces that extend continuously in an axial direction between a distal end 950 and proximal end 951 of the tissue-removing blade member 916. The distal end 950 of the annular tissue-removing blade member 916 is shaped to define a plurality of cutting teeth, generally indicated at 924. In the illustrated embodiment, the distal end 950 of the annular tissue-removing blade 916 is shaped to define eight cutting teeth 924. Each cutting tooth 924 includes a leading surface 942 and a trailing surface 948 that meet at a distal tip. The distal tips of each of the cutting teeth 924 are positioned in a cutting plane. The trailing surface 948 of each cutting tooth 924 is formed at a relief angle relative the cutting plane. The leading surface 942 of each cutting tooth 924 is formed at a positive rake angle and fleam angle.

Figure 23:
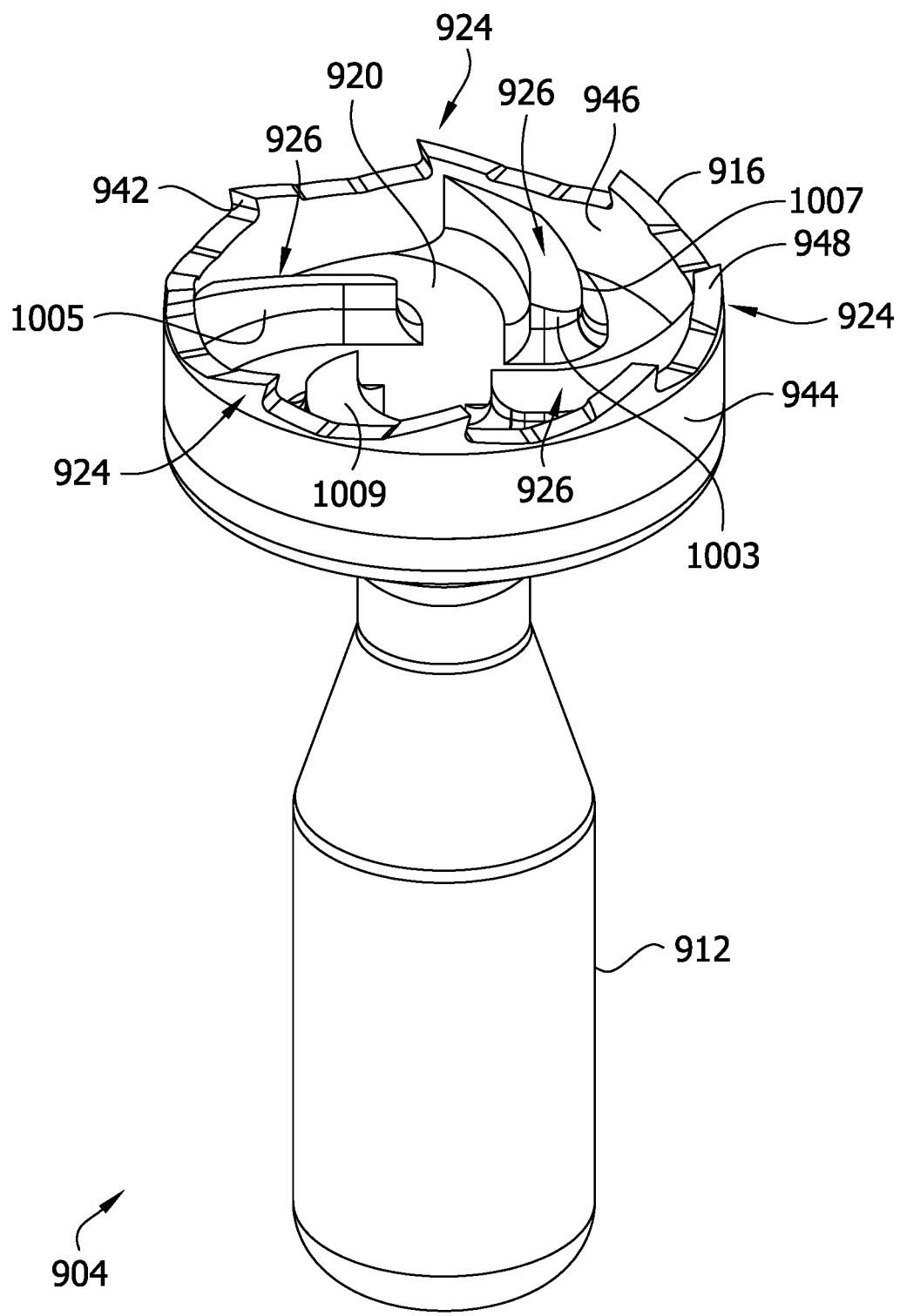
FIG. 23 is a perspective of the tissue-removing element of FIG. 22.

Referring to FIG. 23, the annular tissue-removing blade member 916 is configured to be secured to the tissue-removing element body member 912 to form a tissue-removing element 904. The annular tissue-removing blade member 916 is sized so that the proximal end 951 thereof sits against the annular shoulder 927. When the annular tissue-removing blade member 916 is seated against the annular shoulder 927, the radially inner surface 946 engages the radially outwardly facing portion of the annular shoulder 927 and the radially outer surfaces 1001 of the inner shearing members 926. Likewise, the proximal end 951 engages the axially distal facing portion of the annular shoulder 927. Preferably, the radially outer ends of the shearing members 926 extend distally to shear tissue after it is separated from the body lumen wall by the adjacent leading cutting tooth 924. The annular tissue-removing blade member 916 is secured to the tissue-removing element body member 912 so that the radially outermost end of the leading surface 1005 of each inner shearing member 926 slightly trails the radially innermost end of the leading surface 942 of a cutting tooth 924 (e.g., by between about $0/\pi$ radians and about $45/\pi$ radians). The orientation of the shearing members 926 with respect to the cutting teeth maximizes the distal reach of the radially outer end of the shearing member so that the shearing member is capable of shearing as much of the cut tissue as possible. The annular tissue-removing blade member 916 can be secured to the tissue-removing element body 912 using one or more of welds, adhesives, mechanical fasteners, or other suitable forms of securement.

Referring again to FIG. 22, in one method of making the tissue-removing element 904, the annular tissue-removing blade member 916 is machined from a tubular length of material. The annular tissue-removing blade member 916 can be made from any suitable material including, for example, 465 stainless steel, 17-4 stainless steel, MP35N alloy, 35N LT alloy, titanium, and blends thereof. Other materials, such as other types of stainless steel, nickel, cobalt, chromium molybdenum, tungsten carbide, plastic, or combinations thereof, can also be used without departing from the scope of the invention. In one or more embodiments the annular tissue-removing blade member 916 is made from a harder material than the tissue-removing element body member 912. In certain embodiments the cutting teeth 924 are formed by laser cutting the annular tissue-removing blade member 916 from a length of tubular material. The tissue-removing element body member 912 is preferably formed as a one-piece body of material, using a cutting implement to remove material from a blank. Any suitable material can be used for the tissue-removing element body member 912 including, for example, 465 stainless steel, 17-4 stainless steel, MP35N alloy, 35N LT alloy, titanium, and blends thereof. Other materials, such as other types of stainless steel, nickel, cobalt, chromium molybdenum, tungsten carbide, plastic, or combinations thereof, can also be used without departing from the scope of the invention. Preferably, the leading surface 1005, trailing surface 1007, and radially inner surface 1003 of each of the inner shearing members 926 and the planar axial end surface 920 are formed by removing material from a blank using a cutting implement that is positioned at a fixed axial depth relative the tissue-removing element body member 912. Once the annular tissue-removing blade member 916 and tissue-removing element body member 912 are formed, they are secured together so that the proximal end 951 of the tissue-removing blade member sits against the annular shoulder 927 of the tissue-removing element body member. In certain embodiments, the tissue-removing blade member 916 is welded to the tissue-removing element body member 912.

Figure 24:
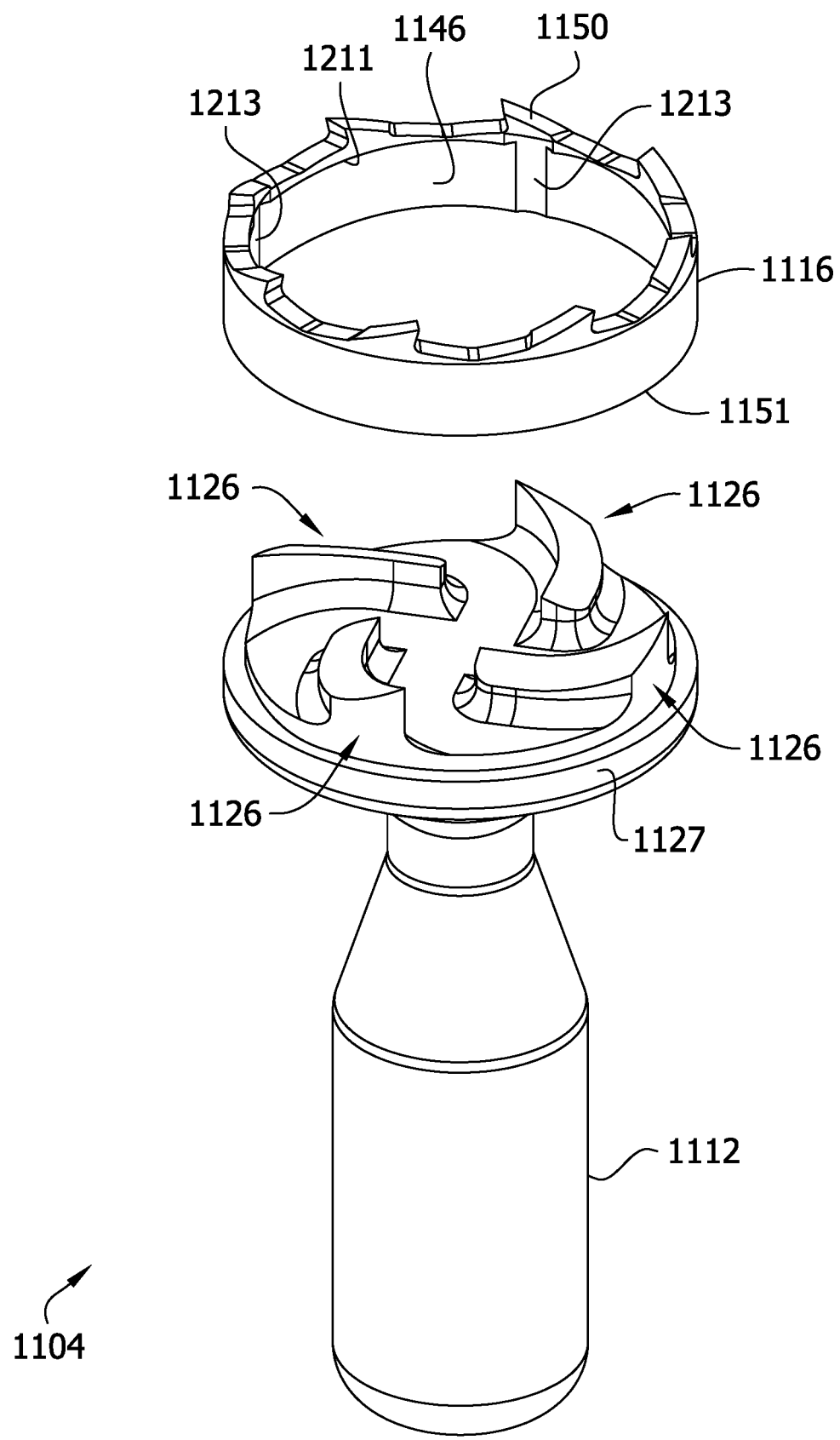
FIG. 24 is an exploded perspective of another tissue-removing element.
Figure 25:
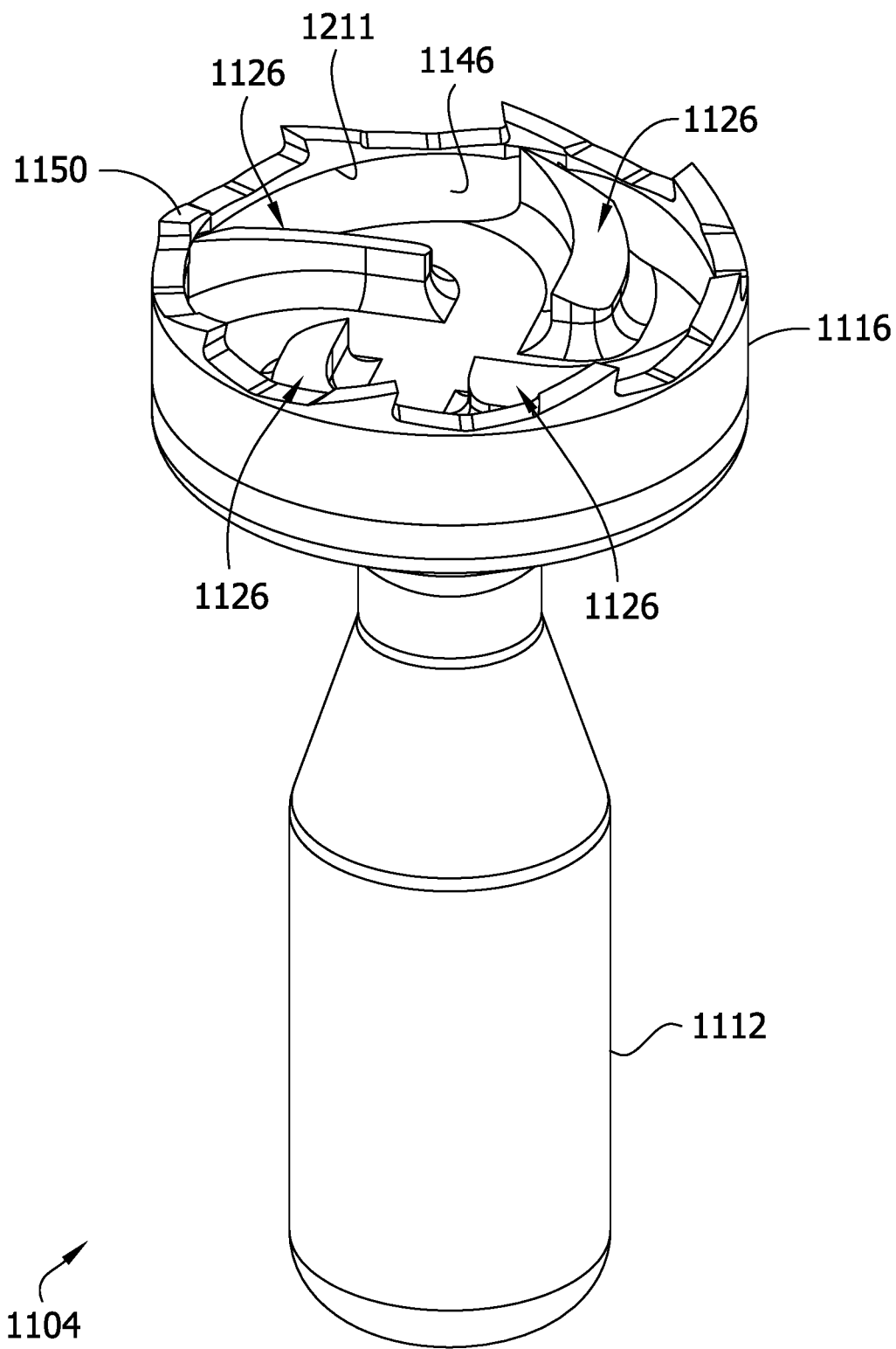
FIG. 25 is perspective of the tissue-removing element of FIG. 24.

As illustrated in FIGS. 24-25, a tissue-removing element 1104 is substantially similar to the tissue-removing element 904, except for the differences that are, in part, apparent and, in part, pointed out hereinafter. Features of the tissue-removing element 1104 are given the reference number of corresponding features of the tissue-removing element 904, plus 200. Like the tissue-removing element 904, the tissue-removing element 1104 comprises a separate tissue-removing element body member 1112 and annular tissue-removing blade member 1116. However, the radially inner surface 1146 of the annular tissue-removing blade member 1116 is not an annular surface that extends continuously in an axial direction between the distal end 1150 and proximal end 1151 of the annular tissue-removing blade member. Instead, the radially inner surface 1146 is undercut to have an annular shoulder 1211 adjacent the distal end 1150 of the tissue-removing blade member 1116. In addition, the radially inner surface 1146 includes radial grooves 1213 that extend axially from adjacent the distal end 1150 of the tissue-removing blade member 1116 toward the proximal end 1151 thereof. The undercut formed by the annular shoulder 1211 and the grooves 1213 provide extra clearance for fitting the annular tissue-removing blade member 1116 to the tissue-removing element body member 1112. In particular, it is contemplated that the annular grooves 1213 will be angularly aligned with the radially outermost portion of the inner shearing members 1126 to provide clearance for any portion of the inner shearing members that extends radially past the radially outwardly facing portion of the annular shoulder 1127.

Figure 26:
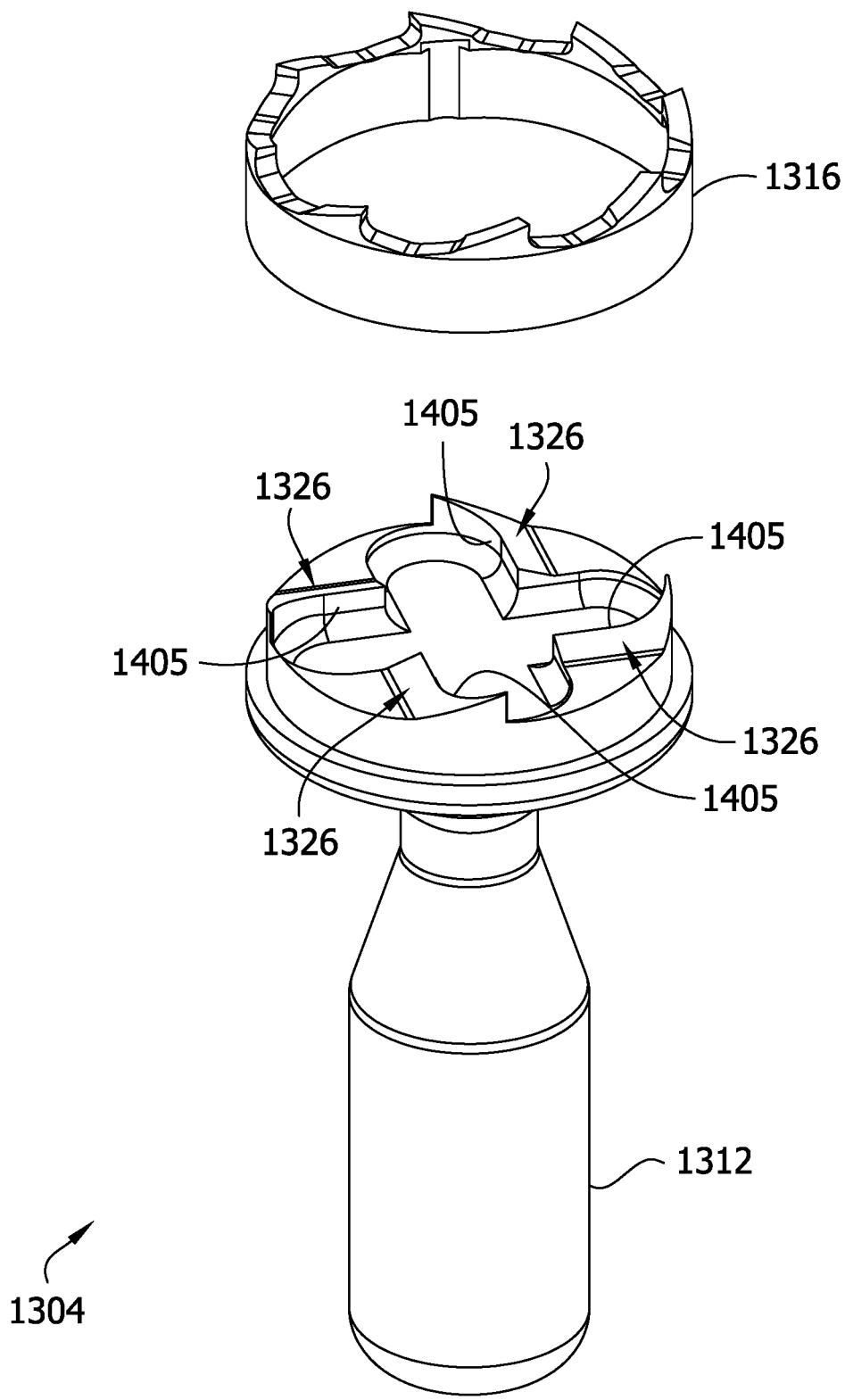
FIG. 26 is an exploded perspective of another tissue-removing element.
Figure 27:
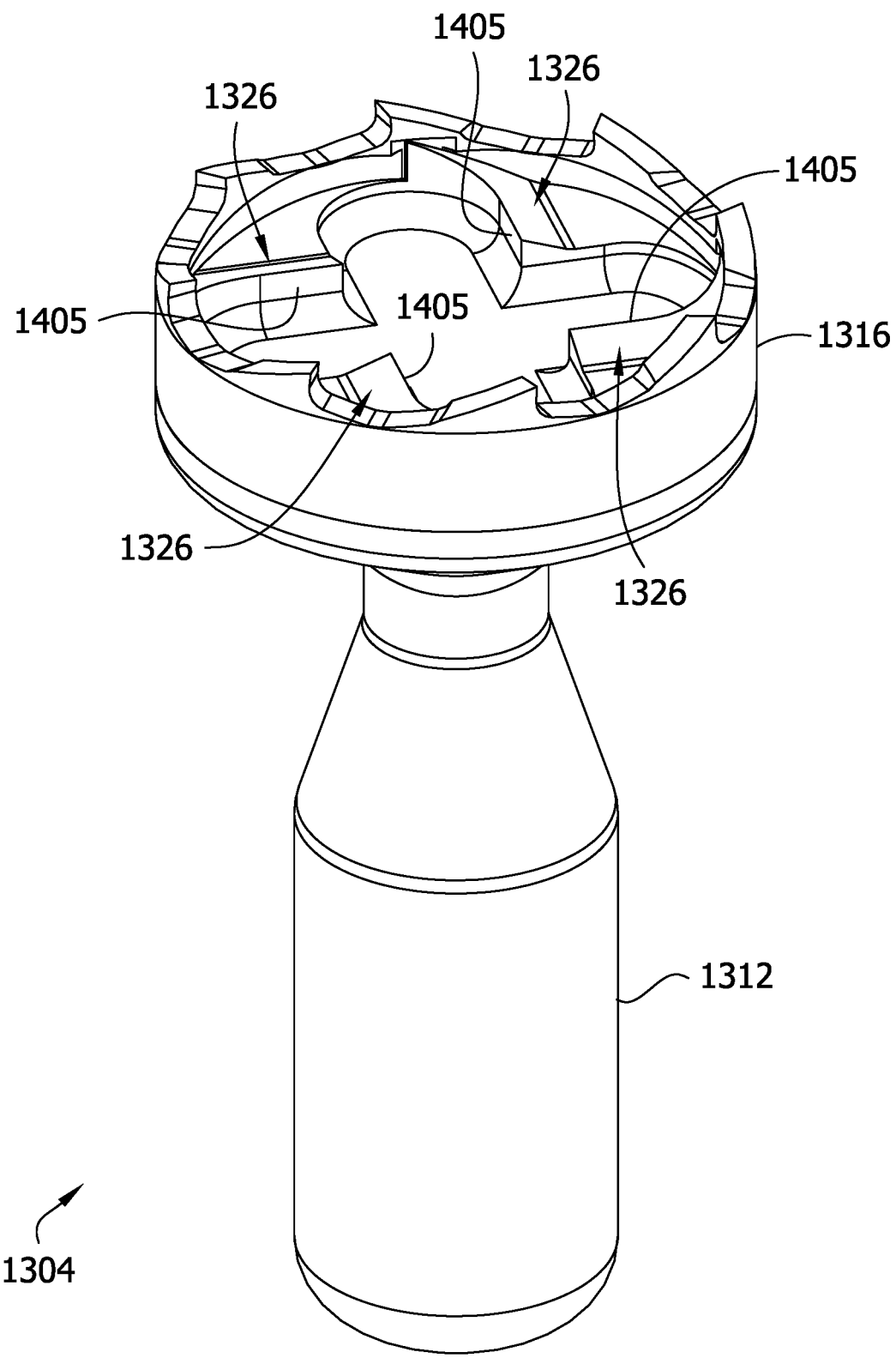
FIG. 27 is perspective of the tissue-removing element of FIG. 26.

Referring to FIGS. 26-27, a tissue-removing element 1304 is substantially similar to the tissue-removing element 1104, except for the differences that are, in part, apparent and, in part, pointed out hereinafter. Features of the tissue-removing element 1304 are given the reference number of corresponding features of the tissue-removing element 1104, plus 200. Like the tissue-removing element 1104, the tissue-removing element 1304 is formed by securing a tissue-removing element body member 1312 to a separate annular tissue-removing blade member 1316. Unlike the tissue-removing element body member 1112, the leading surfaces 1405 of the inner shearing members 1326 are formed by machining a cross cut into the distal end of the tissue-removing element body member 1312.

Where dimensional ranges are cited in the present disclosure, it should be understood that the range is inclusive of the end points of the range, unless otherwise indicated. For example, a range of "between about 1 inch and about 2 inches" includes lengths of about 1 inch and about 2 inches and all of the lengths between those two end points of the range.

When introducing elements of the present invention or the one or more embodiment(s) thereof, the articles "a", "an", "the" and "said" are intended to mean that there are one or more of the elements. The terms "comprising", "including"

and "having" are intended to be inclusive and mean that there may be additional elements other than the listed elements.

As various changes could be made in the above apparatuses, systems, and methods without departing from the scope of the invention, it is intended that all matter contained in the above description and shown in the accompanying drawings shall be interpreted as illustrative and not in a limiting sense.

What is claimed is:

1. A tissue-removing catheter for removing tissue from a body lumen, the tissue-removing catheter comprising:
    a rotatable shaft; and
    a tissue-removing element coupled to the rotatable shaft for rotating the tissue-removing element in a cutting direction about an axis of rotation, the tissue-removing element having opposite first and second axial ends and comprising:
        an annular cutting blade extending around the axis of rotation at the first axial end of the tissue-removing element; and
        an inner shearing member formed into the first axial end of the tissue-removing element radially inward of the annular cutting blade, the inner shearing member comprising a leading surface having a radially outer, arcuate portion and a radially inner, generally planar portion defining a radially inner end of the inner shearing member, the radially outer, arcuate portion extending from a radially outer end thereof adjacent a radially inner surface of the annular cutting blade in a direction substantially tangential to the radially inner surface of the annular cutting blade to a radially inner end thereof, said radially outer, arcuate portion curving radially inwardly toward the axis of rotation between the radially outer and radially inner ends thereof, said radially inner, generally planar portion extending linearly in a generally radially inward direction from the radially inner end of said radially outer, arcuate portion to the radially inner end of the shearing member and being oriented in a plane, the plane being offset from the axis of rotation in a direction perpendicular to the plane;
    wherein the radially inner, generally planar portion faces generally in a leading circumferential direction with respect to the axis of rotation;
    wherein the radially outer, arcuate portion extends radially inwardly and circumferentially in a trailing circumferential direction opposite the leading circumferential direction along an entire extent from the radially outer end of the radially outer, arcuate portion to the generally planar portion.

2. A tissue-removing catheter as set forth in claim 1 wherein the annular cutting blade has an outer radius and the plane is offset from the axis of rotation in a direction perpendicular to the plane a distance, said distance being from about 10% to about 70% of the outer radius of the annular cutting blade.

3. A tissue-removing catheter as set forth in claim 2 wherein the radially inner, generally planar portion of the inner shearing member has a length, said length being from about 1% to about 75% of the outer radius of the annular cutting blade.

4. A tissue-removing catheter as set forth in claim 2 wherein a radially innermost location of the inner shearing member is spaced apart from an outer surface of the annular cutting blade along a radius of the annular cutting blade a radial length, said radial length being from about 10% to about 80% of the outer radius of the annular cutting blade.

5. A tissue-removing catheter as set forth in claim 1 wherein the inner shearing member is configured and arranged to impact tissue in the body lumen at an obtuse angle as the tissue-removing element rotates in the cutting direction in the body lumen.

6. A tissue-removing catheter as set forth in claim 1 wherein the annular cutting blade comprises a plurality of cutting teeth.

7. A tissue-removing catheter as set forth in claim 6 wherein each of the cutting teeth has a negative rake angle.

8. A tissue-removing catheter as set forth in claim 6 wherein the annular cutting blade comprises from about 24 cutting teeth to about 48 cutting teeth.

9. A tissue-removing catheter as set forth in claim 6 wherein each of the cutting teeth comprises a leading surface and an axial end surface, each leading surface being oriented at about a ninety-degree angle to the respective axial end surface.

10. A tissue-removing catheter as set forth in claim 1 wherein the annular cutting blade comprises a plurality of serrations.

11. A tissue-removing catheter as set forth in claim 10 wherein each serration comprises a radially outer edge and a radially inner edge, the radially outer and radially inner edges being arcuate and extending respectively from a leading end proximally to a nadir and from the respective nadir distally to a trailing end.

12. A tissue-removing catheter as set forth in claim 11 wherein the nadir of the radially inner edge is located proximal of the nadir of the radially outer edge.

13. A tissue-removing catheter as set forth in claim 12 wherein a concave axial end surface extends between the radially outer edge and the radially inner edge.

14. A tissue-removing catheter as set forth in claim 1 wherein the annular cutting blade comprises a plurality of merlon shaped cutting teeth and a plurality of crenel shaped gaps interleaved between the plurality of merlon shaped cutting teeth.

15. A tissue-removing catheter as set forth in claim 14 wherein each of the merlons comprises a leading surface partially defining an adjacent leading crenel, an end portion of the leading surface extending axially.

16. A tissue-removing catheter as set forth in claim 15 wherein the end portion of the leading surface is substantially planar and oriented at a positive fleam angle.

17. A tissue-removing catheter as set forth in claim 1 wherein a cross-shaped recess is formed in the first axial end of the tissue-removing element, said cross-shaped recess defining four inner shearing members.

* * * * *